United States Patent [19]

Matsutani et al.

[11] Patent Number: 4,927,829
[45] Date of Patent: May 22, 1990

[54] HETEROCYCLIC COMPOUNDS AND ANTIULCER AGENTS

[75] Inventors: Shigeru Matsutani; Yukio Mizushima, both of Osaka, Japan

[73] Assignee: Shionogi & Co., Ltd., Osaka, Japan

[21] Appl. No.: 306,752

[22] Filed: Feb. 6, 1989

[30] Foreign Application Priority Data

Feb. 18, 1988 [JP]  Japan .................................. 63-36130

[51] Int. Cl.$^5$ ................... C07D 487/02; A61K 31/495
[52] U.S. Cl. ....................................... 514/258; 544/282
[58] Field of Search ......................... 544/282; 514/258

[56] References Cited

FOREIGN PATENT DOCUMENTS 218423  4/1987  European Pat. Off. .

Primary Examiner—Mukund J. Shah
Assistant Examiner—C. L. Csen

Attorney, Agent, or Firm—Wenderoth, Lind & Ponack

[57] ABSTRACT

Novel heterocyclic compounds of the formula:

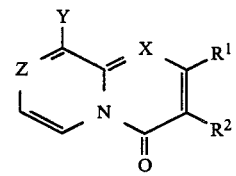

or pharmaceutically acceptable acid addition salts thereof having a more potent and longer lasting cytoprotective anti-ulcer action than known analogues, useful in the treatment or prophylaxis of gastric ulcer at an oral dose of 10–500 mg, preferably 20 mg–100 mg per day to an adult, are provided through several routes.

25 Claims, No Drawings

HETEROCYCLIC COMPOUNDS AND ANTIULCER AGENTS

BACKGROUND OF THE INVENTION

1. Field of the Invention

The present invention relates to novel heterocyclic compounds exhibiting excellent antiulcer action.

2. Prior Art

Compounds which have gastroprotective action have been disclosed, for example, in U.S. Pat. No. 3,070,623 and U.S. Pat. No. 4,335,048. Moreover, compounds having a pyridopyrimidine ring are disclosed in U.S. Pat. No. 4,457,932 and EP. Pat. Publn. A-218,423.

Prior to the present application, the present inventors filed EP. Pat. Publn. A-218,423 disclosing serial compounds having a pyridopyrimidine ring with potent gastroprotective activities. Some of those have aromatic heterocyclic groups at the 9-position of the ring. On the other hand, the present invention involves, as an aspect, pyridopyrimidine-type compounds, some of which have also heterocyclic group. However, the heterocyclic groups of the present invention are aliphatic ones such as morpholinocarbonyl, piperazinocarbonyl or thiomorpholinocarbonyl, and therefore they differ from those of the prior art in this sense. Moreover, the compounds of the present invention are stabler in alkali and show more potent activities over a longer period of time.

SUMMARY OF THE INVENTION

The present invention directed to heterocyclic compounds having excellent anti-ulcer activities of the formula:

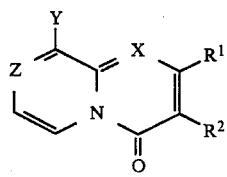
(I)

wherein $R^1$ and $R^2$ each is identically or differently hydrogen, $C_1$-$C_4$ alkyl, cyano, tetrazolyl, carboxy or $C_1$-$C_4$ alkyloxycarbonyl; X and Z each is identically or differently CH or N; and Y is $C_1$-$C_4$ alkylthio, —CH$_2$SAr, —S—S—Ar, —SCOR$^3$, —SCH$_2$R$^3$ or —SC(=NOH)Ar, where Ar is optionally substituted phenyl, optionally substituted thienyl or $C_1$-$C_4$ alkyloxycarbonyl; $R^3$ is

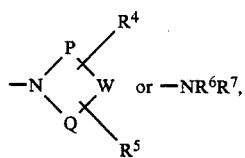

where $R^4$ and $R^5$, which may be bound to any of P, Q and W, each is identically or differently hydrogen, optionally substituted $C_1$-$C_4$ alkyl or optionally substituted phenyl or $R^4$ and $R^5$ taken together may form a condensed benzene ring; P and Q each is identically or differently $C_1$-$C_4$ alkylene; W is single bond or —O—, —S— or optionally substituted —NH—; and $R^6$ and $R^7$ each is identically or differently $C_1$-$C_4$ alkyl (provided that $R^1$ must be hydrogen and $R^2$ be tetrazolyl or cyano when Y is —SCONR$^6$R$^7$) or pharmaceutically acceptable acid addition salts thereof.

DESCRIPTION OF THE PREFERRED EMBODIMENT

Development of such compounds as to show enhanced anti-ulcer activity with less adverse effect has been desired. The inventors have found that the compounds of the formula (I) or their salts exhibit excellent anti-ulcer activities. Thus, the present invention has been established. The present invention relates to compounds of the formula:

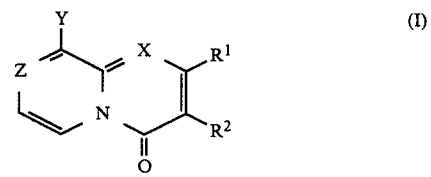
(I)

wherein $R^1$ and $R^2$ each is identically or differently hydrogen, $C_1$-$C_4$ alkyl, cyano, tetrazolyl, carboxy or $C_1$-$C_4$ alkyloxycarbonyl; X and Z each is identically or differently CH or N; and Y is $C_1$-$C_4$ alkylthio, —CH$_2$SAr, —S—S—Ar, —SCOR$^3$, —SCH$_2$R$^3$ or —SC(=NOH)Ar, where Ar is optionally substituted phenyl, optionally substituted thienyl or $C_1$-$C_4$ alkyloxycarbonyl; $R^3$ is

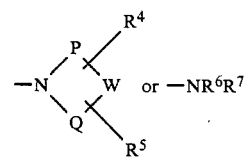

where $R^4$ and $R^5$, which may be bound to any of P, Q and W, each is identically or differently hydrogen, optionally substituted $C_1$-$C_4$ alkyl or optionally substituted phenyl or $R^4$ and $R^5$ taken together may form a condensed benzene ring; P and Q each is identically or differently $C_1$-$C_4$ alkylene; W is single bond or —O—, —S— or optionally substituted —NH—; and $R^6$ and $R^7$ each is identically or differently $C_1$-$C_4$ alkyl (provided that $R^1$ must be hydrogen and $R^2$ be tetrazolyl or cyano when Y is —SCONR$^6$R$^7$) or pharmaceutically acceptable acid addition salts thereof.

In the specification, $C_1$-$C_4$ alkyl means straight or branched chain $C_1$-$C_4$ alkyl, including methyl, ethyl, n-propyl, isopropyl, n-butyl, sec-butyl, isobutyl, tert-butyl, and the like.

Optionally substituted phenyl means substituted or unsubstituted phenyl, where substituents include halogen such as fluorine, chloride, bromine and iodine, $C_1$-$C_4$ alkoxy, $C_1$-$C_4$ alkoxycarbonyl, cyano, nitro and trifluoromethyl. Phenyl may be substituted by 1 or 2 of those substituents.

Optionally substituted thienyl means substituted or unsubstituted thienyl, whose substituents include $C_1$-$C_4$ alkyl.

Optionally substituted alkyl means substituted or unsubstituted alkyl, whose substituents include phenyl which may be substituted by halogen, isopropylcarbamoyl or methylenedioxy.

Optionally substituted —NH— represents substituted or unsubstituted —NH—, and R⁴ or R⁵ can be substituted thereto.

The heterocyclic compounds of formula (I) may be prepared according to the following methods.

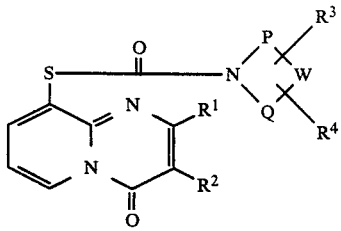

(wherein Hal means halogen, and $R^1$, $R^2$, $R^4$, $R^5$, P, Q, W, X and Z have the same meaning as defined above.)

9-Mercapto compound (II) is allowed to react with carbamoyl halide (VII) in an appropriate solvent at 10°–100° C., preferably at a temperature (10°–30° C.) around room temperature for 10 minutes-10 hours, if necessary in the presence of a base, whereby the objective substance (I a) is obtained.

The carbamoyl halide (VII) used for the reaction is obtained by reacting the corresponding amine (VIII) with a carbamoylation agent such as trichloromethyl chloroformate in an appropriate solvent.

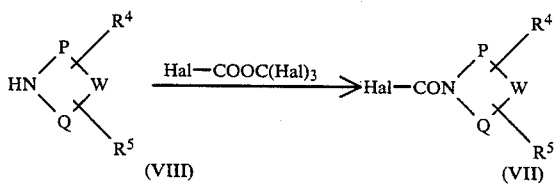

(wherein Hal, $R^4$, $R^5$, P, Q and W have the same meaning as defined above.)

As the base used for the reaction there are exemplified inorganic bases such as sodium carbonate, potassium carbonate, sodium hydroxide, potassium hydroxide or sodium hydride and organic bases such as triethylamine, isopropylethylamine, N-methylpyrrolidine, N-ethylpiperidine, morpholine, pyridine, etc.

As the solvent used for the reaction, there are exemplified halogenated hydrocarbon such as methylene chloride, 1,2-dichloroethane, chloroform or carbon tetrachloride, hydrocarbons such as cyclopentane, cyclohexane or n-hexane; benzene; ethyl acetate; acetonitrile; tetrahydrofuran; hexamethylphosphoric triamide; dimethylformamide; dimethylacetamide or dimethyl sulfoxide; and ketones such as acetone, methyl ethyl ketone, etc.

Method B

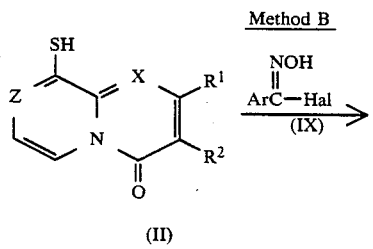

Method B

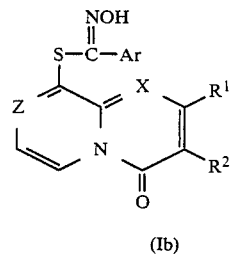

(wherein Ar, Hal, $R^1$, $R^2$, X and Z have the same meaning as defined above)

9-Mercapto compound (II) is allowed to react with arylhydroxymoyl halide (IX) in dry methylene chloride at a cooling temperature (e.g. −50°–10° C.) for several ten minutes to several hours in the presence of a base, whereby the objective substance (Ib) is obtained.

As the base used for the reaction there are exemplified organic bases such as triethylamine or pyridine and inorganic bases such as sodium carbonate, potassium carbonate, sodium hydride, potassium hydroxide or sodium hydroxide.

Method C

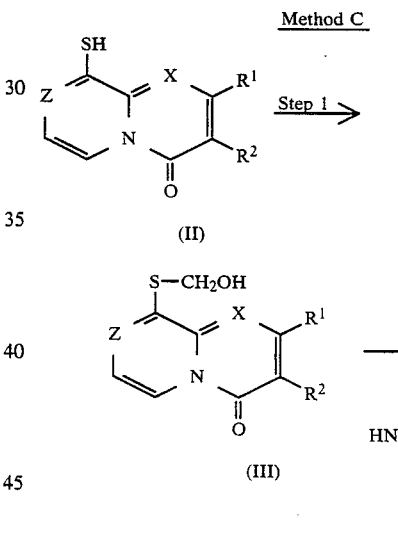

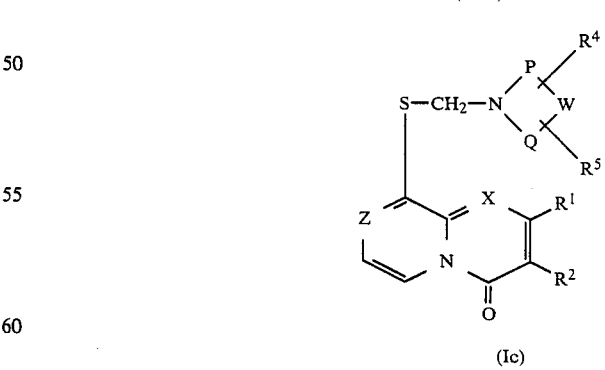

(wherein $R^1$, $R^2$, $R^4$, $R^5$, P, Q, X, Z and W have the same meaning as defined above.)

Step 1

9-Mercapto compound (II) is allowed to react with formaldehyde in an appropriate solvent at 80°–200° C., preferably at 90°–100° C. for 1–10 hours under nitrogen atmosphere, whereby the compound (III) is obtained. As the solvent used for the reaction there are exemplified halogenated hydrocarbons such as dichloromethane, 1,2-dichloroethane, chloroform or carbon tetrachloride; hydrocarbons such as cyclopentane, cyclohexane, n-hexane; or benzene; ethyl acetate; acetonitrile; tetrahydrofuran; and ketones such as acetone, methyl ethyl ketone, and the like.

Step 2

The compound (III) obtained is allowed to react with the amine (VIII) in an appropriate solvent such as tetrahydrofuran, methylene chloride or the like for few hours in the presence of a dehydrating agent such as magnesium sulfate, whereby the objective compound (I c) is obtained.

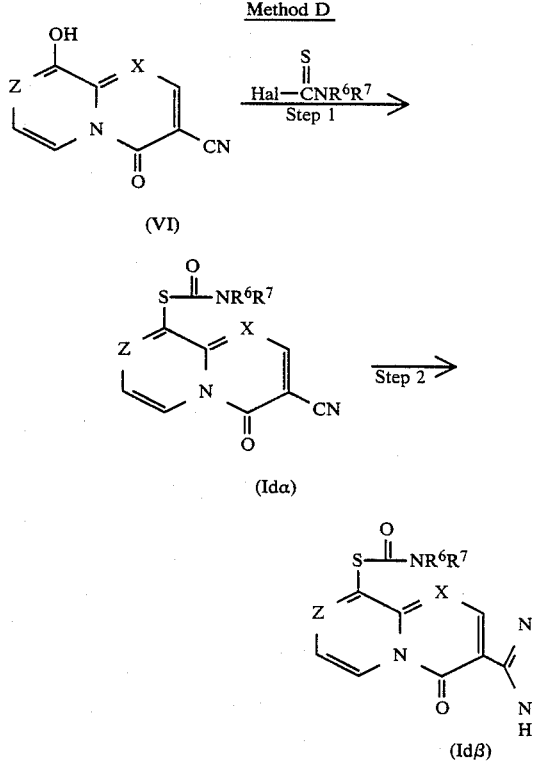

(wherein Hal, $R^6$, $R^7$, X and Z have the same meaning as defined above.)

Step 1

Compound (VI) is allowed to react with dialkylthiocarbamoyl halide in an appropriate solvent at about 10°–100° C., preferably at a temperature (10°–30° C.) around room temperature for 10 minutes–10 hours in the presence of a base, followed by heating at about 100° to 250° C., whereby the objective compound (I dα) is obtained.

As the base used for the reaction there are exemplified inorganic bases such as sodium carbonate, potassium carbonate, sodium hydroxide, potassium hydroxide or sodium hydride and organic bases such as triethylamine, isopropylethylamine, N-methyl pyrrolidine, N-ethylpiperidine, morpholine or pyridine.

As the solvent used for the reaction there are exemplified halogenated hydrocarbons such as methylene chloride, 1,2-dichloroethane, chloroform or carbon tetrachloride; hydrocarbons such as cyclopentane, cyclohexane or n-hexane; benzene; ethyl acetate; acetonitrile; tetrahydrofuran; ketones such as acetone, methylethyl ketone, or the like.

Step 2

The obtained compound (I dα) is allowed to react, at a temperature of from 10 to about 100° C. for about 10 to 20 hours, with $Al(N_3)_3$ which was previously prepared by the reaction of aluminium chloride with sodium azide under cooling, whereby the objective compound (I dβ) is obtained.

As the solvent used for the reaction there are exemplified dimethylformamide, dimethylacetamide, methylene chloride, 1,2-dichloroethane, chloroform, carbon tetrachloride; benzene; tetrahydrofuran; acetonitrile, and the like. Further, the reaction can be promoted by adding an acid catalyst such as Lewis acid.

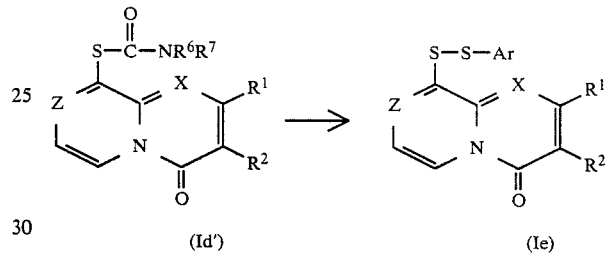

(wherein Ar, $R^1$, $R^2$, $R^6$, $R^7$, X and Z have the same meaning as defined above)

The compound (I d') is allowed to react with sulphenyl halide in an appropriate solvent at 10°–100° C., preferably at a temperature around room temperature for 10 minutes–10 hours in the presence of zinc halide, whereby the objective compound (I e) is obtained.

As the solvent used for the reaction there are exemplified halogenated hydrocarbons such as methylene chloride, 1,2-dichloroethane, chloroform or carbon tetrachloride; hydrocarbons such as cyclopentane, cyclohexane, n-hexane or benzene; ethyl acetate; acetonitrile and tetrahydrofuran.

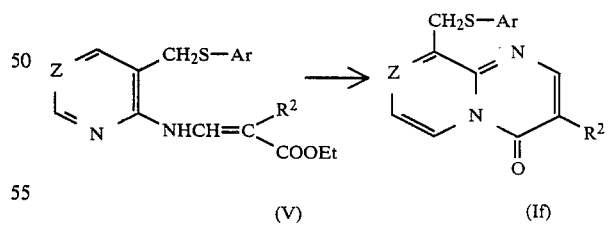

(wherein Ar, $R^2$ and Z have the same meaning as defined above)

Compound (V) is subjected to condensation reaction in an appropriate solvent in the presence of an acid condensation agent, whereby the objective compound (I f) is obtained.

The acid condensation agents illustratively include polyphosphoric acid, alkanoic acid such as acetic acid or propionic acid, and their mixture.

The same solvents as illustrated in Method A may be used in this reaction.

The objective compounds (I) of this invention is convertible into their pharmaceutically acceptable salts. Depending upon the kind of the substituent, they can be converted into alkali metal salts (lithium, sodium or potassium salt), alkaline earth metal salts (calcium or magnesium salt). Besides, the objective compounds can be sometimes converted into acid addition salts. In this case, the acids usable here refer to inorganic acids such as hydrochloric acid, hydrobromic acid or phosphoric acid, and organic acids such as acetic acid, oxalic acid, maleic acid, fumaric acid, citric acid, malic acid, adipic acid or succinic acid.

The objective compounds (I) of this invention and/or their pharmaceutically acceptable salts can be orally or parenterally administered to humans or animals. For example, compounds (I) are orally administered in the form of tablet, granule, powder, capsule or liquid, or parenterally administered in the form of injection or suppository. These formulations are manufactured by use of additives such as excipient, binder, disintegrator, lubricant, stabilizer, corrective, suspending agent, dispersant, solubilizer and antiseptics according to a well-known method. The excipients include illustratively lactose, sucrose, starch, cellulose, sorbit, etc. Binders include gum arabic, gelatin, polyvinyl-pyrrolidone, etc. Lubricants include magnesium stearate, talc, silica gel, etc.

When the objective compounds (I) of this invention are used in the treatment for peptic ulcer, they may be administered orally or parenterally to an adult at a dose of 100–500 mg, preferably 20–100 mg per day in one or several divided doses.

The following examples, reference examples and formulation are shown to clarify the practical embodiment of this invention.

The abbreviations used in the examples, reference examples and tables shall have the following meanings.

Me: methyl,
Et: ethyl;
TCF: trichloromethyl chloroformate;
Et₃N: triethylamine;
THF: tetrahydrofuran;
EtOH: ethanol
ZnCl₂: zinc chloride
t-Bu: tert-butyl
n-BuLi: n-butyllithium
DMF: dimethylformamide
EMM: diethyl ethoxymethylenemalonate
n-Bu₃P: n-butylphosphine
DMAP: 4-dimethylaminopyridine
n-PrSH: n-propylmercaptane
HMPA: hexamethylphosphoric triamide

EXAMPLE 1

3-Ethoxycarbonyl-9-(4-morpholinocarbonylthio)-4-oxo-4H-pyrido[1,2-a]pyrimidine (I a-1)

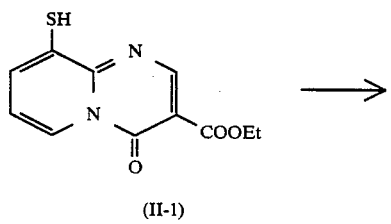

(II-1)

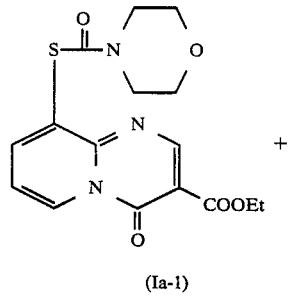

(Ia-1)

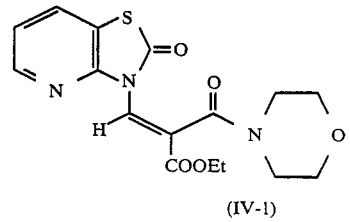

(IV-1)

To a solution of 1.0 g (4 mmol) of 3-ethoxycarbonyl-9-mercapto-4-oxo-4H-pyrido[1,2-a]pyrimidine (II-1) in 40 ml of dry methylene chloride is added 0.24 ml (2 mmol) of trichloromethyl chloroformate, and the resultant mixture is stirred for 10 min. and concentrated at room temperature. To the residue are added 60 ml of dry methylene chloride, 0.77 ml (44 mmol) of diisopropyl ethylamine and 0.37 ml (44 mmol) of morpholine, and the mixture is stirred at room temperature for 4 hours. The reaction mixture is washed with N—HCl, saturated aqueous NaHCO₃ and water in order. After the organic layer is dried, the solvent is distilled off under reduced pressure. The residue is washed with a small amount of ethyl acetate to give 197 mg of crude product I a-1. The mother liquor is evaporated to dryness, and the residue is chromatographed on a column of silica gel eluting with ethyl acetate to give 75 mg of crude product I a-1 and 387 mg of IV-1. The crude products I a-1 are combined and recrystallized from chloroform-n-hexane to give 157 mg of pure product I a-1.

m.p. 191°–194° C. (dec),

Anal Calcd. of I a-1 (%) for C₁₆H₁₇N₃O₅S. 1/5H₂O: C, 52.36; H, 4.78; N, 11.45; S, 8.74; Found (%): C, 52.35; H, 4.72; N, 11.24; S, 8.74:

The crude IV-1 is recrystallized from ethyl acetate to give 145 mg of pure product IV-1. m.p. 160°–162° C. (dec).

Anal Calcd. of IV-1 (%) for C₁₆H₁₇N₃O₅S: C, 52.88; H, 4.72; N, 11.56; S, 8.82; Found (%): C, 52.79; H, 4.80; N, 11.42; S, 8.83.

EXAMPLE 2

3-Ethoxycarbonyl-9-[(1-(2-methoxyphenyl)piperazine-4-yl)-carbonylthio]-4-oxo-4H-pyrido[1,2-a]pyrimidine (I a-2)

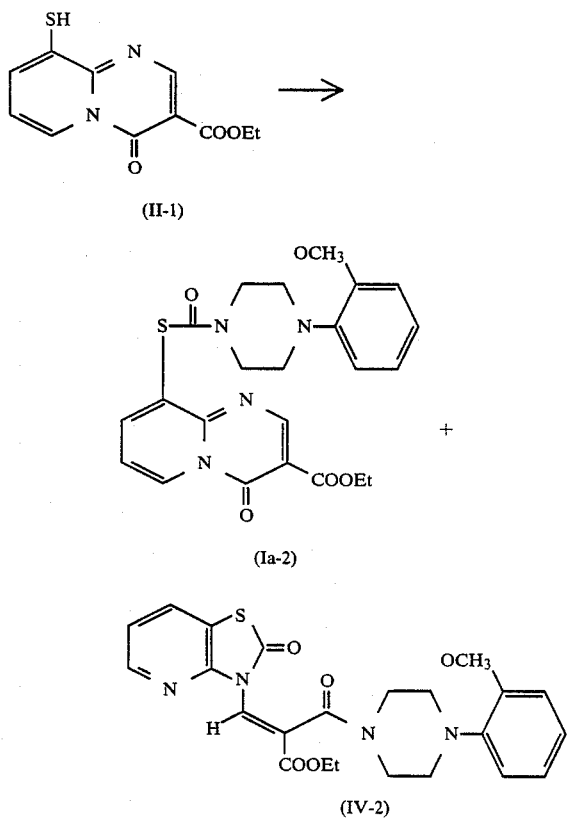

To a solution of 1.0 g (4 mmol) of 3-ethoxycarbonyl-9-mercapto-4-oxo-4H-pyrido[1,2-a]pyrimidine (II-1) in 40 ml of dry methylene chloride is added 0.24 ml (2 mmol) of trichloromethyl chloroformate, and the resultant mixture is stirred for 10 min. and concentrated at room temperature under atmospheric pressure. To the residue are added 60 ml of dry methylene chloride and 0.77 ml (44 mmol) of 4-(2-methoxyphenyl)piperazine under ice-cooling, and the reaction mixture is stirred for 1 hour at room temperature. The reaction mixture is washed with N—HCl, saturated aqueous NaHCO$_3$ and water in order, and the organic layer is dried and concentrated under reduced pressure. The oily residue in 1.94 g is chromatographed on a column of silica gel eluting with ethyl acetate to give 45 mg of Ia-2 (m.p. 154°–156° C. recrystallized from chloroform-n-hexane) and 516 mg of IV-2 (m.p. 151°–153° C. recrystallized from ethyl acetate).

Anal Calcd. of Ia-2 (%) for $C_{23}H_{24}N_4O_5S$: C, 58.96; H, 5.16; N, 11.96; S, 6.84; Found (%): C, 59.04; H, 5.38; N, 11.54; S, 6.82.

Anal Calcd. of IV-2 (%) for $C_{23}H_{24}N_4O_5S$: C, 58.96; H, 5.16; N, 11.96; S, 6.84; Found (%): C, 58.99; H, 5.19; N, 11.79; S, 6.85.

EXAMPLES 3-4

To a solution of the substituted mercapto compound (II) in dry methylene chloride (a ml of the solvent) is added trichloromethyl chloroformate, and the solution is stirred at room temperature for 10-30 minutes (h$_1$: reaction time). The solvent is evaporated under atmospheric pressure. To the residue is added dry methylene chloride (b ml of the solvent), and subsequently an appropriate amine is added in the presence or absence of a base, and the mixture is stirred at room temperature for 1.5–2.5 hours (h$_2$: reaction time). The reaction mixture is washed with N—HCl, saturated aqueous NaHCO$_3$ and water in order. And the organic layer is dried over sodium sulfate, and then the solvent is evaporated under reduced pressure. The residue is purified by recrystallization from appropriate solvent or by a column chromatography affording the desired Products (I a).

Details of the reaction conditions for manufacturing Compounds (I a) (structure of reactants and their amount, kind of solvents, reaction time) and the structure and physical constants (melting point, elementary analysis) of the objective compounds (I a) obtained are shown in Table 1.

TABLE 1
(Method A)

Reaction of compound (II) with (VIII) to give (Ia):

HN−P(R⁴)−W−Q(R⁵) (VIII) reacts with mercapto-pyridopyrimidinone (II) to give sulfonamide (Ia).

| Example No. | R¹ | R² | HN−P−W−Q−R⁵ (VIII) | Amount II (g) | Amount VIII (g) | TCF (ml) | Et₃N (ml) | Solvent CH₂Cl₂ (a) (ml) | Solvent (b) (ml) | Reaction Time h₁ (min) | Reaction Time h₂ (hr) | Product (Yield, %) | Melting Point (°C) | Molecular Formula | Elementary Analysis (%) Found / Calcd. C | H | N | S |
|---|---|---|---|---|---|---|---|---|---|---|---|---|---|---|---|---|---|---|
| 3 | COOEt | CH₃ | morpholine (HN−O) | 1.0 | 0.33 | 0.23 | — | 40 | 60 | 30 | 2.0 | I a (9.7) | 130–132 | C₁₇H₁₉N₃O₅S | 54.01 / 54.10 | 5.10 / 5.07 | 11.05 / 11.13 | 8.57 / 8.50 |
| 4 | H | COOEt | thiomorpholine (HN−S) | 1.0 | 0.44 | 0.24 | 0.55 | 40 | 60 | 10 | 2.5 | I a (15.5) | 187–189 | C₁₆H₁₇N₃O₄S₂ | 50.66 / 50.64 | 4.50 / 4.52 | 10.92 / 11.07 | 16.78 / 16.90 |

EXAMPLE 5

3-Ethoxycarbonyl-9-[(4-piperonylpiperazine-1-yl)carbonylthio]-4-oxo-4H-pyrido[1,2-a]pyrimidine (I a-3)

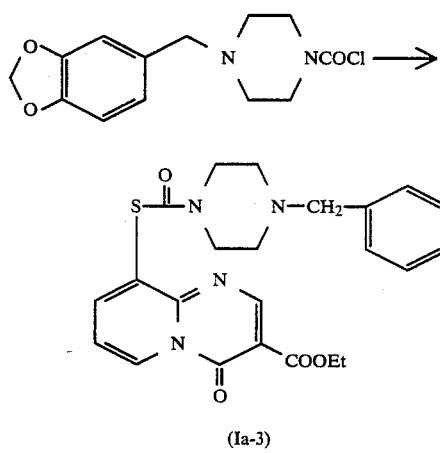

A solution of 0.48 ml (4 mmol) of trichloromethyl chloroformate in 30 ml of dry tetrahydrofuran is stirred at room temperature for 3 hours. The reaction mixture is cooled with ice water, and a solution of 1.8 g (8 mmol) of piperonylpiperazine in 10 ml of dry tetrahydrofuran is dropwise added. The reaction mixture is stirred at room temperature for 1 hour. A solution of 3.3 ml (24 mmol) of triethylamine in 5 ml of tetrahydrofuran is added under cooling with ice water. The reaction mixture is stirred at room temperature for 1 hour. To the mixture is added 1.0 g (4 mmol) of 9-mercapto compound (II-1) in the solid form in one portion and the resulting mixture is stirred at room temperature overnight. The resulting suspension is filtered to remove the precipitate. The filtrate is concentrated under reduced pressure to give 3.66 g of the crude product, which is chromatographed on silica gel eluting with ethyl acetate to give 1.4 g (70.6%) of the titled compound (I a-3). m.p. 159°–161° C. (chloroform-n-hexane).

Anal Calcd. (%) for $C_{24}H_{24}N_4O_6S \cdot 1/5H_2O$: C, 57.63; H, 4.92; N, 11.20; S, 6.41; Found (%): C, 57.64; H, 4.79; N, 11.05; S, 6.59.

EXAMPLES 6–21

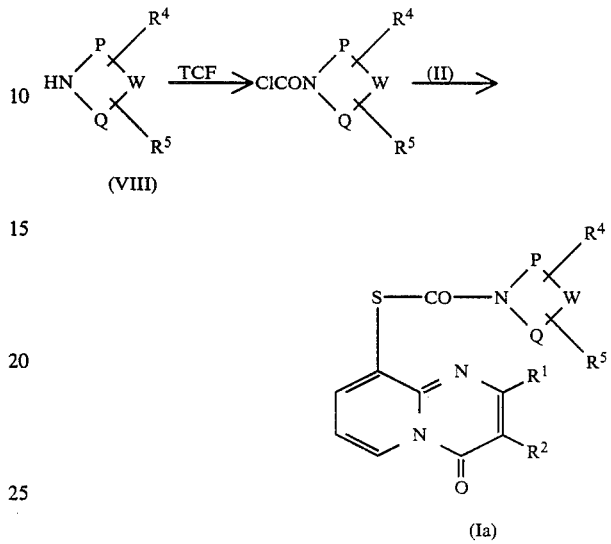

A solution of trichloromethyl chloroformate in dry tetrahydrofuran is heated at 60° C. for 1–3 hours (reaction time $h_1$). The mixture obtained is cooled with ice water and a solution of the appropriate amine (VIII) in 5 ml of dry tetrahydrofuran is dropwise added. Then the reaction mixture is stirred for 1–2.5 hours (reaction time $h_2$) at room temperature. Subsequently a solution of triethylamine in 5 ml of dry tetrahydrofuran is dropwise added to the mixture under ice cooling. The reaction mixture is stirred at room temperature for 0.5–1 hour (reaction time $h_3$). Then the substituted 9-mercapto compound (II) is added in the solid form and the resulting mixture is stirred at room temperature for 3–117 hours (reaction time $h_4$). The suspension obtained is filtered and the precipitate is filtrated. The filtrate is concentrated under reduced pressure, and the residue is chromatographed on a column of silica gel to give the titled compound (I a).

Details of the reaction conditions for manufacturing compound (I a) (structure of reactants and their amount, solvent, reaction time) and the structure and physical constants (melting point, elementary analysis) of the objective compound (I a) obtained are shown in Table 2.

TABLE 2
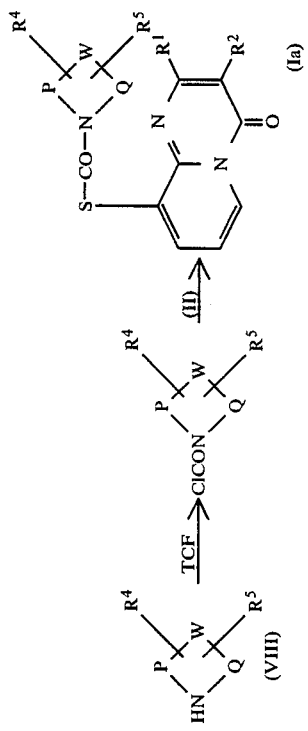
(Ia)
| Example No. | R¹ | R² | (VIII) | Amount II (g) | VIII (ml) | TCF (ml) | Et₃N (ml) | Solvent THF (ml) | Reaction Time (hr) h₁ h₂ h₃ h₄ | Product (Yield) (%) | Melting Point (°C.) | Molecular Formula | Elementary Analysis (%) Upper column: Found Lower column: Calcd. C H N S |
|---|---|---|---|---|---|---|---|---|---|---|---|---|---|
| 6 | H | H | HN⟨⟩NCH₂CONHCHMe₂ | 1.0 | 2.1 | 0.67 | 4.6 | 30 | 1  1  1  68 | 36.1 | 152–154 | $C_{18}H_{23}N_5O_3S$ | 55.38  5.97  17.86  8.11<br>55.51  5.95  17.98  8.23 |
| 7 | H | H | 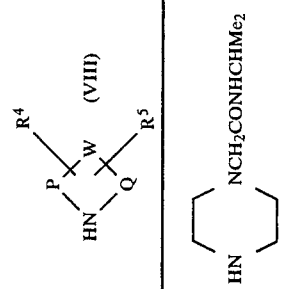 | 1.0 | 1.13 | 0.67 | 4.6 | 30 | 2  1.5  0.5  18 | 49.6 | 181–184 | $C_{13}H_{13}N_3O_2S_2$·1/10H₂O | 50.45  4.29  13.51  20.61<br>50.50  4.30  13.59  20.74 |
| 8 | H | H | 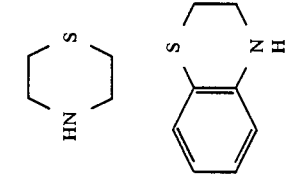 | 1.0 | 1.7 | 0.67 | 4.6 | 30 | 1.5  1  0.5  19 | 91.3 | 164–166 | $C_{17}H_{13}N_3O_2S_2$ | 57.25  3.75  11.78  17.94<br>57.44  3.69  11.82  18.04 |
| 9 | H | H | 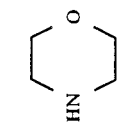 | 1.0 | 0.98 | 0.67 | 4.6 | 30 | 2.5  1  1  20 | 89.3 | 167–169 | $C_{13}H_{13}N_3O_3S$ | 53.53  4.54  14.36  11.19<br>53.59  4.50  14.43  11.01 |

TABLE 2-continued $$\underset{(VIII)}{HN\underset{P}{\overset{R^4}{\diagup}}\underset{Q}{\overset{W}{\diagdown}}R^5} \xrightarrow{TCF} ClCON\underset{P}{\overset{R^4}{\diagup}}\underset{Q}{\overset{W}{\diagdown}}R^5 \xrightarrow{(II)} \text{(Ia)}$$

(Ia)

| Example No. | R¹ | R² | (VIII) | Amount II (g) | VIII (ml) | TCF (ml) | Et₃N (ml) | Solvent THF (ml) | Reaction Time (hr) h₁ h₂ h₃ h₄ | Product (Yield) (%) | Melting Point (°C.) | Molecular Formula | Elementary Analysis (%) Upper column: Found Lower column: Calcd. C  H  N  S |
|---|---|---|---|---|---|---|---|---|---|---|---|---|---|
| 10 | H | H | ![indoline] | 1.0 | 1.3 | 0.67 | 4.6 | 30 | 1 2 1 20 | 79.4 | 233–235 | C₁₇H₁₃N₃O₂S | 63.34 4.16 12.96 9.82 / 63.14 4.05 13.00 9.92 |
| 11 | H | H | ![o-methoxyphenylpiperazine] | 1.0 | 2.2 | 0.67 | 4.6 | 50 | 1 1 0.5 3 | 10.3 | 173–174 | C₂₀H₂₀N₄O₃S | 60.33 5.16 13.90 7.87 / 60.59 5.09 14.13 8.09 |
| 12 | H | H | ![4-chlorobenzyl piperazine] | 1.0 | 3.2 | 0.67 | 4.6 | 30 | 1 5 1 20 | −100 | foam | C₂₆H₂₃N₄O₂SCl | M⁺(m/e) 490 |
| 13 | H | COOEt | ![piperidine] | 1.0 | 0.79 | 0.48 | 3.3 | 30 | 2 1 1 18 | 69.9 | 153–155 | C₁₇H₁₉N₃O₄S | 56.33 5.32 11.58 8.86 / 56.49 5.30 11.63 8.87 |

TABLE 2-continued $$HN\underset{P}{\overset{R^4}{\diagup}}\underset{Q}{\overset{W}{\diagdown}}R^5 \quad (VIII)$$

$$\xrightarrow{TCF} ClCON\underset{P}{\overset{R^4}{\diagup}}\underset{Q}{\overset{W}{\diagdown}}R^5 \xrightarrow{(II)}$$

(Ia)

| Example No. | R¹ | R² | (VIII) | Amount II (g) | VIII (ml) | TCF (ml) | Et₃N (ml) | Solvent THF (ml) | Reaction Time (hr) h₁ h₂ h₃ h₄ | Product (Yield) (%) | Melting Point (°C.) | Molecular Formula | Elementary Analysis (%) Upper column: Found Lower column: Calcd. C H N S |
|---|---|---|---|---|---|---|---|---|---|---|---|---|---|
| 14 | H | COOEt | (thiomorpholine, HN-S ring) | 1.0 | 0.63 | 0.48 | 3.3 | 30 | 2 1 1 17 | 88.3 | 188-190 | C₁₅H₁₅N₃O₄S₂ | 49.11 4.31 11.42 17.38 / 49.30 4.14 11.50 17.55 |
| 15 | H | COOEt | (tetrahydroisoquinoline) | 1.0 | 1.0 | 0.48 | 3.3 | 30 | 2 1 1 19 | 99 | 162-164 | C₂₁H₁₉N₃O₄S | 61.59 4.74 10.15 7.67 / 61.60 4.68 10.26 7.83 |
| 16 | H | COOEt | (piperazine, HN-NH) | 1.0 | 0.67 | 0.48 | 3.3 | 30 | 3 1 1 90 | 16.2 | 215-216 | C₁₆H₁₇N₃O₄S · 1/5H₂O | 54.69 4.84 11.76 8.90 / 54.75 5.00 11.97 9.14 |
| 17 | H | H | (thiazolidine, HN-S ring) | 1.0 | 0.88 | 0.67 | 4.6 | 30 | 1.5 1 1 18 | 80.6 | 189-192 | C₁₂H₁₃N₃O₂S₂ · 1/5H₂O | 48.41 3.86 14.11 21.86 / 48.53 3.87 14.15 21.60 |
| 18 | H | H | (piperidine, HN) | 1.0 | 1.1 | 0.67 | 4.6 | 30 | 2 1 1 18 | 96.1 | 96.0-97.0 | C₁₄H₁₅N₃O₂S | 58.13 5.21 14.47 11.07 / 58.11 5.22 14.52 11.08 |

TABLE 2-continued $$\text{HN}\diagdown\!\!\!\!\!\!\!\underset{Q}{\overset{P}{\diagup}}\!\!\!\!\!\!\!\diagup\!\!\!\!\!\!\!\underset{R^5}{\overset{R^4}{W}} \text{ (VIII)} \quad \xrightarrow{\text{TCF}} \text{ClCON}\diagdown\!\!\!\!\!\!\!\underset{Q}{\overset{P}{\diagup}}\!\!\!\!\!\!\!\diagup\!\!\!\!\!\!\!\underset{R^5}{\overset{R^4}{W}} \text{ (II)} \longrightarrow \text{(Ia)}$$

(Ia)

| Example No. | R¹ | R² | (VIII) | Amount II (g) | VIII (ml) | TCF (ml) | Et₃N (ml) | Solvent THF (ml) | Reaction Time (hr) h₁ | h₂ | h₃ | h₄ | Product (Yield) (%) | Melting Point (°C.) | Molecular Formula | Elementary Analysis (%) Upper column: Found Lower column: Calcd. C H N S |
|---|---|---|---|---|---|---|---|---|---|---|---|---|---|---|---|---|
| 19 | H | H | pyrrolidine | 1.0 | 0.94 | 0.67 | 4.6 | 30 | 2.5 | 1 | 1 | 15 | 99.7 | 149–151 | C₁₃H₁₃N₃O₃S | 56.69 4.78 15.05 11.38 / 56.71 4.76 15.26 11.65 |
| 20 | H | COOEt | 2,6-dimethylmorpholine | 1.0 | 0.98 | 0.48 | 3.3 | 30 | 3 | 1 | 0.5 | 18 | 85 | cis 148–150 / trans 149–151 | C₁₈H₂₁N₃O₅S / C₁₈H₂₁N₃O₅S | 55.16 5.42 10.61 8.10 / 55.23 5.41 10.74 8.19 / 55.15 5.41 10.70 8.14 / 55.23 5.41 10.74 8.19 |
| 21 | H | COOEt | 2-ethylmorpholine | 0.5 | 0.46 | 0.24 | 1.2 | 15 | 2 | 1 | 1 | 17 | 56.9 | 157–159 | C₁₈H₂₁N₃O₄S·H₂O | 55.09 5.39 10.68 8.37 / 54.95 5.89 10.68 8.15 |

EXAMPLE 22

3-Ethoxycarbonyl-9-[(l-4-methoxycarbonylthiazolizine-3-yl)carbonylthio]-4-oxo-4H-pyrido[1,2-a]pyrimidine (I a-4)

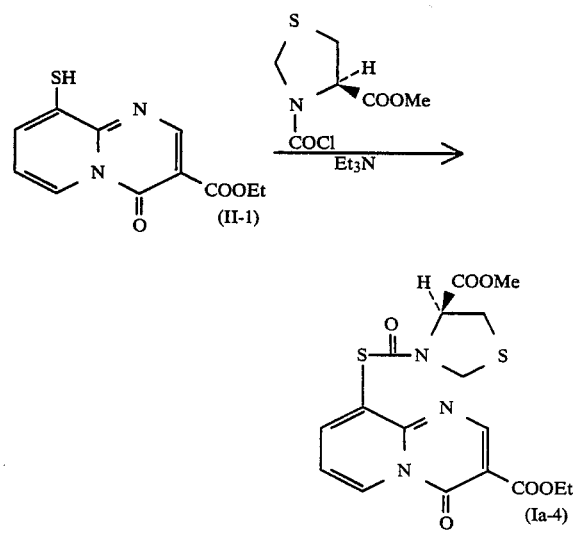

To a solution of 1.0 g (4 mmol) of 9-mercapto compound II-1 in 20 ml of dry methylene chloride are added 0.92 mg (4.4 mmol) of 3-chlorocarbonyl-l-thiazolizine-4-methylcarboxylate and 0.5 g (4.9 mmol) of triethylamine and the resultant mixture is stirred at room temperature for 3 hours. The reaction mixture is evaporated under reduced pressure and the residue is distributed in chloroform-5% aqueous sodium bicarbonate. The organic layer is washed with saturated brine, dried over Na2SO4, and concentrated at reduced pressure to give 2.5 g of the crude product, which is chromatographed on a column of silica gel eluting with ethyl acetate to give 1.398 g (Yield: 82.6%) of Ia-4. And the product I a-4 is recrystallized from ethyl ether-ethyl acetate to give colorless needles.

m.p. 124°–125° C.

Anal Calcd. (%) for $C_{17}H_{17}N_3O_6S_2$: C, 48.22; H, 4.05; N, 9.92; S, 15.14; Found (%): C, 48.26; H, 4.20; N, 9.80; S, 14.98.

EXAMPLE 23

9-[(l-4-Methoxycarbonylthiazolidine-3-yl)carbonylthio]-4-oxo-4H-pyrido[1,2-a]pyrimidine (I a-5)

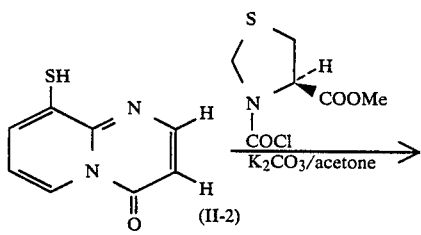

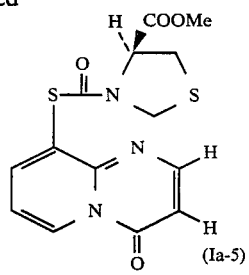

To a mixture of 0.5 g (2.8 mmol) of 9-mercapto compound (II-2), 0.58 g (4.2 mmol) of potassium carbonate and 30 ml of dry acetone is added 0.62 g (2.96 mmol) of methyl 3-chlorocarbonyl-l-thiazolidine-4-carboxylate at room temperature, and the resultant mixture is stirred for 70 hours. The resultant suspension is filtered, and the filtrate is concentrated under reduced pressure to give 1.69 g of crude oil. The product is chromatographed on a column of silica gel eluting with ethyl acetate to give 0.949 g of the titled compound I a-5 as tacky oil. Mass spectrum: M/e 351 (M+)

EXAMPLE 24

3-Ethoxycarbonyl-9-[(p-fluorophenyl)carbohydroxymoyl)thio]-4-oxo-4H-pyrido[1,2-a]pyrimidine (Ib-1)

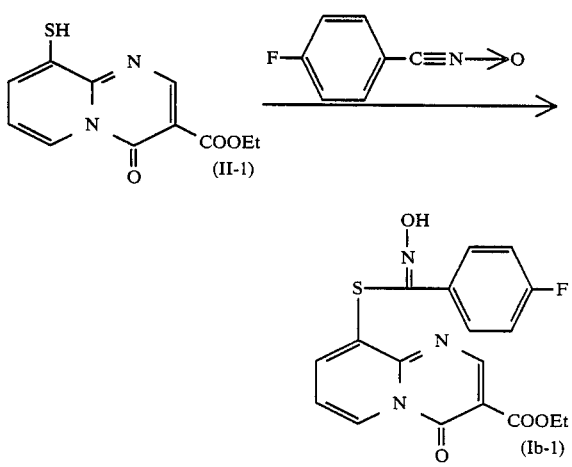

A mixture of 0.38 g (2.2 mmol) of p-fluorobenzonitrile oxide and 0.5 g (2 mmol) of 9-mercapto compound (II-1) is dissolved in 10 ml of dry methylene chloride, and a solution of 0.34 ml of triethylamine in 5 ml of dry methylene chloride is dropwise added at −20° C. The solution is stirred at room temperature for 24 hours and concentrated under reduced pressure, and the residue is distributed in chloroform-water. The organic layer is dried and concentrated under reduced pressure. The residue is crystallized from ethyl acetate to give 0.55 g (71.1%) of the titled compound I b-1.

m.p. 171°–175° C. (dec).

Anal Calcd. (%) for $C_{18}H_{14}N_3O_4SF$: C, 55.81; H, 3.64; N, 10.85; S, 8.28; F, 4.90; Found (%): C, 55.91; H, 3.63; N, 10.67; S, 8.51; F, 4.69.

EXAMPLE 25–40

Mercapto compound (II) is allowed to react with the corresponding arylhydroxymoyl chloride (IX) in the same manner as Example 24, to give the products (I b) shown in the table 3.

TABLE 3

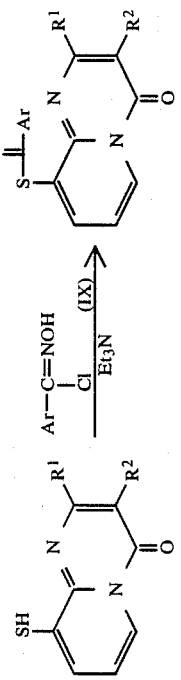

| Example No. | R¹ | R² | Ar | Amount II (g) | IX (g) | Et₃N (ml) | Solvent CH₂Cl₂ (ml) | Reaction Time (hr) | Product (Yield) (%) | Melting Point (°C.) | Molecular Formula | Elementary Analysis (%) Upper column: Found / Lower column: Calcd. C | H | N | S | Hal |
|---|---|---|---|---|---|---|---|---|---|---|---|---|---|---|---|---|
| 25 | H | COOEt | 4-Cl-C₆H₄ | 0.54 | 0.45 | 0.36 | 10 | 2 | 47.1 | 171–173 | C₁₈H₁₄N₃O₄SCl | 53.57 / 53.53 | 3.67 / 3.49 | 10.24 / 10.41 | 7.99 / 7.94 | 8.55 / 8.78 (Hal:Cl) |
| 26 | H | COOEt | 4-CO₂Me-C₆H₄ | 0.5 | 0.47 | 0.34 | 15 | 1 | 60.7 | 180–182 (dec) | C₂₀H₁₇N₃O₆S·2/5 THF | 56.63 / 56.86 | 4.51 / 4.46 | 9.20 / 9.21 | 7.07 / 7.03 | |
| 27 | H | COOEt | C₆H₅ | 0.5 | 0.34 | 0.34 | 15 | 1 | 81.2 | 161–163 | C₁₈H₁₅N₃O₄S·½H₂O | 57.51 / 57.13 | 3.97 / 4.26 | 10.88 / 11.11 | 8.17 / 8.47 | |
| 28 | H | COOEt | 2,3-Cl₂-C₆H₃ | 0.7 | 0.63 | 1.0 | 30 | 1.5 | 70.5 | 178–180 | C₁₈H₁₃N₃O₄SCl₂ | 49.20 / 49.33 | 3.09 / 2.99 | 9.52 / 9.59 | 7.51 / 7.31 | 16.17 / 16.18 (Hal:Cl) |
| 29 | H | COOEt | 3-CH₃-thien-2-yl | 0.4 | 0.31 | 0.2 | 10 | 1.5 | 62.7 | 158–162 (dec) | C₁₇H₁₅N₃O₄S₂·⅓CHCl₃ | 48.52 / 48.49 | 3.61 / 3.60 | 9.65 / 9.79 | 14.91 / 14.94 | 8.38 / 8.26 (Hal:Cl) |
| 30 | H | COOEt | 4-CF₃-C₆H₄ | 0.8 | 0.72 | 1.0 | 30 | 4.0 | 48.3 | 139–140 | C₁₉H₁₄N₃O₄SF₃ | 52.27 / 52.17 | 3.43 / 3.23 | 9.71 / 9.61 | 7.33 / 7.33 | 13.32 / 13.02 (Hal:F) |

TABLE 3-continued

Reaction scheme:

Structure (II): pyridine with SH and N=C(R¹)-C(R²)=... with C=O and N, reacting with Ar-C(Cl)=NOH (IX) / Et₃N to give (Ib): same pyridine core with S-C(=NOH)-Ar substituent.

| Example No. | R¹ | R² | Ar | Amount II (g) | Amount IX (g) | Et₃N (ml) | Solvent CH₂Cl₂ (ml) | Reaction Time (hr) | Product (Yield) (%) | Melting Point (°C) | Molecular Formula | Elementary Analysis (%) Upper: Found / Lower: Calcd. C | H | N | S | Hal |
|---|---|---|---|---|---|---|---|---|---|---|---|---|---|---|---|---|
| 31 | COOEt | CH₃ | 4-F-C₆H₄ | 0.4 | 0.29 | 0.2 | 10 | 2.5 | 48.1 | 160–162 | $C_{19}H_{16}N_3O_4SF$ | 56.79 / 56.85 | 4.01 / 4.02 | 10.28 / 10.47 | 8.20 / 7.99 | 5.01 / 4.73 (Hal:F) |
| 32 | H | H | 2,6-Cl₂-C₆H₃ | 0.4 | 0.55 | 0.38 | 20 | 4.5 | 46.1 | 168–170 | $C_{16}H_9N_3O_2SCl_2$ | 48.95 / 49.19 | 2.65 / 2.48 | 11.26 / 11.47 | 8.65 / 8.76 | 19.11 / 19.36 (Hal:Cl) |
| 33 | H | H | 4-CN-C₆H₄ | 1.0 | 1.1 | 0.95 | 40 | 1.5 | 55.3 | 183–185 (dec) | $C_{16}H_{10}N_4O_2S$ | 59.79 / 59.61 | 3.12 / 3.13 | 17.19 / 17.38 | 9.78 / 9.95 | |
| 34 | H | H | 4-F-C₆H₄ | 0.4 | 0.43 | 0.38 | 10 | 4.5 | 39.8 | 185–187 (dec) | $C_{15}H_{10}N_3O_2SF$ | 57.15 / 57.13 | 3.41 / 3.20 | 13.27 / 13.33 | 10.37 / 10.17 | 6.03 / 6.03 (Hal:F) |
| 35 | H | H | 4-CF₃-C₆H₄ | 0.4 | 0.55 | 0.38 | 15 | 2.5 | 85.4 | 165–170 (dec) | $C_{16}H_{10}N_3O_2SF_3$ | 52.97 / 52.60 | 3.00 / 2.76 | 11.38 / 11.50 | 8.75 / 8.78 | 15.25 / 15.60 (Hal:F) |

TABLE 3-continued

Reaction scheme:

Compound (II) [pyridine with SH and N=C(R¹)-C(R²)=O fused ring] + Ar—C(Cl)=NOH (IX), Et₃N → Compound (Ib) [pyridine with S-C(Ar)=NOH and N=C(R¹)-C(R²)=O fused ring]

| Example No. | R¹ | R² | Ar | Amount II (g) | Amount IX (g) | Amount Et₃N (ml) | Solvent CH₂Cl₂ (ml) | Reaction Time (hr) | Product (Yield) (%) | Melting Point (°C.) | Molecular Formula | Elementary Analysis (%) Upper column: Found Lower column: Calcd. C | H | N | S | Hal |
|---|---|---|---|---|---|---|---|---|---|---|---|---|---|---|---|---|
| 36 | H | H | 2,4-(OMe)₂-phenyl | 0.4 | 0.53 | 0.38 | 15 | 2 | 42.3 | 183–184 | $C_{17}H_{15}N_3O_4S$ | 57.16 57.13 | 4.43 4.23 | 11.62 11.76 | 8.74 8.97 | |
| 37 | H | H | 4-COOEt-phenyl | 0.4 | 0.37 | 0.37 | 15 | 3 | 31.6 | 154 (dec) | $C_{12}H_{11}N_3O_4S$ | 49.25 49.14 | 3.63 3.78 | 14.37 14.33 | 10.92 10.93 | |
| 38 | H | H | 4-CO₂Me-phenyl | 0.4 | 0.53 | 0.38 | 15 | 3 | 99.3 | 151–155 | $C_{17}H_{13}N_3O_4S$ | 57.67 57.45 | 3.82 3.69 | 11.42 11.83 | 8.77 9.02 | |
| 39 | H | H | 4-NO₂-phenyl | 0.4 | 0.5 | 0.38 | 15 | 1 | 74.2 | 197–198 | $C_{15}H_{10}N_4O_4S$ | 52.79 52.62 | 2.99 2.94 | 16.09 16.37 | 9.33 9.37 | |
| 40 | H | CN | 2,4-Cl₂-phenyl | 0.5 | 0.6 | 0.41 | 30 | 3 | 41.2 | 174 (dec) | $C_{15}H_8N_4O_2SCl_2 \cdot 2/5CHCl_3$ | 45.05 44.87 | 1.91 1.93 | 12.78 12.76 | 7.35 7.30 | 25.54 25.85 (Hal:Cl) |

EXAMPLE 41

3-Ethoxycarbonyl-9-(4-thiomorpholinomethylthio)-4-oxo-4H-pyrido[1,2-a]pyrimidine (I c-1)

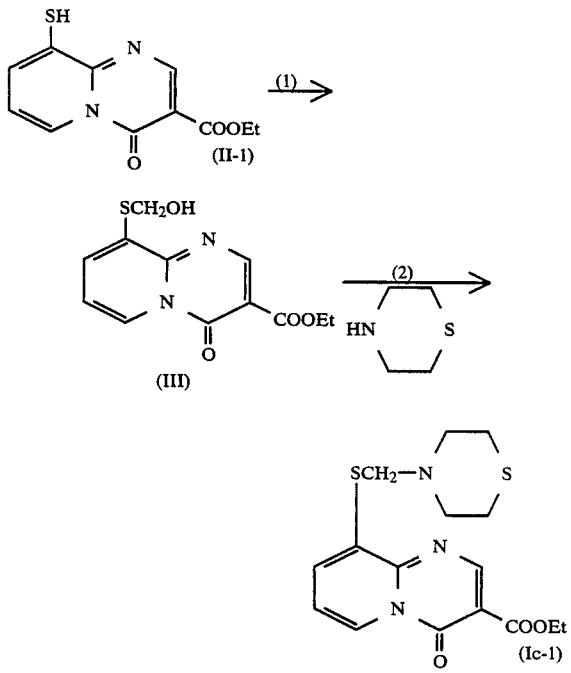

(1) A mixture of 1.0 g of 3-ethoxycarbonyl-9-mercapto-4-oxo-4H-pyrido[1,2-a]pyrimidine (II-1) and 325 mg of 27% formaldehyde is stirred at 100° C. for 2 hours in a nitrogen atmosphere. The reaction mixture is washed with methylene chloride and recrystallized from methylene chloride-methanol (19:1 v/v) to give 311 mg (Yield: 27.8%) of 3-ethoxycarbonyl-9-(hydroxymethylthio)-4-oxo-4H-pyrido[1,2-a]pyrimidine (III).

m.p. 155° C. (dec).

Anal Calcd. (%) for $C_{12}H_{12}N_2O_4S$: C, 51.42; H, 4.32; N, 9.99; S, 11.44; Found (%): C, 51.17; H, 4.31; N, 9.87; S, 11.48.

IR (Nujol): 3424, 3124, 1733, 1667, 1612, 1566 cm$^{-1}$.

NMR (CDCl$_3$-CD$_3$OD, 9:1 v/v) δ: 9.07, 8.05, 7.24 (each 1H, m); 9.05 (1H, s); 5.13, 4.69 (each 1H, s); 4.40 (2H, q, J=7 Hz); 2.57 (1H, br); 1.41 (3H, t, J=7 Hz).

(2) To a mixture of 163 mg of thiomorpholine, 920 mg of magnesium sulfate and 5 ml of tetrahydrofuran is added dropwise a solution of 429 mg of 3-ethoxycarbonyl-9-(hydroxymethylthio)-4-oxo-4H-pyrido[1,2-a]pyrimidine (III) in 25 ml of tetrahydrofuran with stirring under ice-cooling. The reaction mixture is stirred for 1 hour as it is, filtered, and the filtrate is concentrated in vacuo. The residue is recrystallized from ethyl acetatehexane to give 307 mg (Yield: 54.9%) of 3-ethoxycarbonyl-9-(thiomorpholinomethylthio)-4-oxo-4H-pyrido[1,2-a]pyrimidine (I c-1).

m.p. 128°-130° C.

Anal Calcd. (%) for $C_{16}H_{19}N_3O_3S_2$: C, 52.58; H, 5.24; N, 11.50; S, 17.55; Found (%): C, 52.50; H, 5.28; N, 11.42; S, 17.45.

IR (Nujol): 1714, 1693, 1613, 1565 cm$^{-1}$.

NMR (CDCl$_3$) δ: 9.11, 7.96, 7.23 (each 1H, m); 9.10 (1H, s), 4.49 (2H, s); 4.42 (2H, q, J=7 Hz); 2.96, 2.66 (each 4H, m); 1.40 (3H, t, J=7 Hz).

EXAMPLE 42

3-Cyano-9-(dimethylcarbamoylthio)-4-oxo-4H-pyrido[1,2-a]pyrimidine (I d-1)

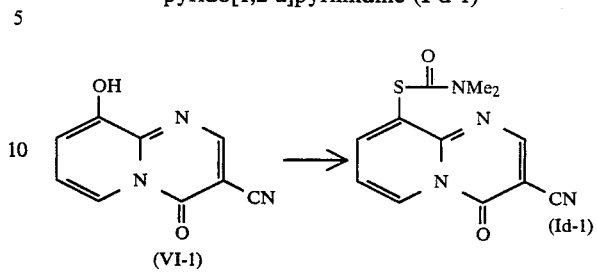

To a mixture of 1 l of dry acetone and 40.8 g (218 mmol) of 3-cyano-9-hydroxy-4-oxo-4H-pyrido[1,2-a]pyrimidine (VI-1) are added 2.7 g (22 mmol) of 4-dimethylaminopyridine and 45.3 ml (327 mmol) of triethylamine. The mixture is mixed with 32.3 g (260 mmol) of dimethylthiocarbamoyl chloride and stirred at room temperature for 27 hours. The reaction mixture obtained is filtered to remove the precipitate. The filtrate is concentrated to dryness under reduced pressure and the residue is distributed in chloroform-N.HCl. The organic layer is washed with water and dried. The solvent is distilled off under reduced pressure. The solid obtained is washed with a small quantity of ethyl acetate to give 41.5 g of a colored solid. The solid obtained is dissolved in 500 ml of Dowtherm A and heated for 5 minutes under reflux. After cooling to room temperature, the mixture is charged in a column of about 300 g of silica gel eluting Dowtherm A with n-hexane and then ethyl acetate to give 16.1 g (Yield: 26.9%) of the product (I d-1).

m.p. 202°-204° C. (ethyl acetate)

Anal Calcd. (%) for $C_{12}H_{10}N_4O_2S$: C, 52.54; H, 3.67; N, 20.43; S, 11.69; Found (%): C, 52.67; H, 3.67; N, 20.19; S, 11.69.

EXAMPLE 43

3-Ethoxycarbonyl-9-(2-nitrophenyldithio)-4-oxo-4H-pyrido[1,2-a]pyrimidine (I e-1)

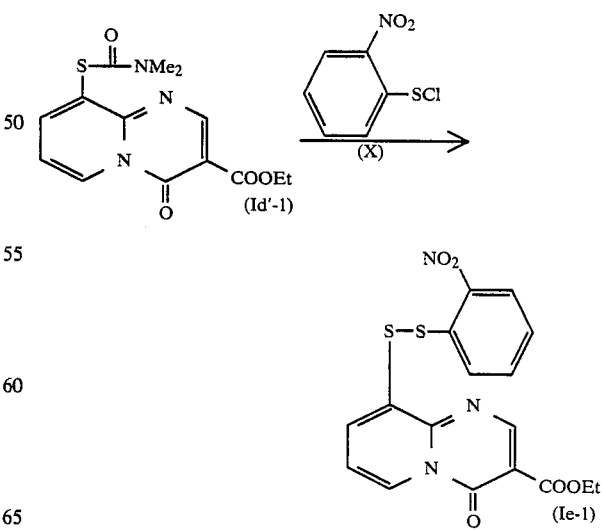

To a solution of 0.32 g (1 mmol) of 3-ethoxycarbonyl-9-(dimethylcarbamoylthio)-4-oxo-4H-pyrido[1,2- a]pyrimidine (I d'-1) in 10 ml of dry 1,2-dichloroethane are added 0.2 g (1.5 mmol) of 2-nitrophenylsulphenyl chloride (X) and 0.2 g (1.5 mmol) of zinc chloride, and the resultant mixture is stirred for 35 minutes at room temperature. After the mixture is diluted with 1,2-dichloroethane, it is washed with N-HCl, 5% NaHCO$_3$ and saturated brine in order. The organic layer is dried over sodium sulfate and concentrated under reduced pressure. The residue in 0.5 g is recrystallized from ethyl acetate-methylene chloride to give 0.365 g (Yield: 90.9%) of the titled compound (I e-1).

m.p. 191°–193° C. (acetonitrile).

Anal Calcd. (%) for $C_{17}H_{13}N_3O_5S_2$: C, 50.61; H, 3.25; N, 10.42; S, 15.89; Found (%): C, 50.64; H, 3.32; N, 10.31; S, 15.85.

EXAMPLES 44–48

The reaction procedure in Example 43 is repeated except that other thiolcarbamate compounds (I d') are used instead of I d'-1, whereby the derivatives shown in Table 4 are obtained.

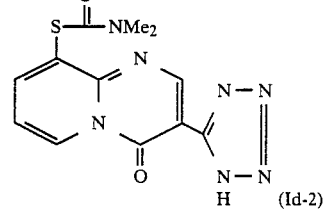

To a suspension of 0.83 g (12.8 mmol) of sodium azide in 30 ml of dry tetrahydrofuran is added 0.63 g (2.7 mmol) of aluminium chloride at −30° C. and the mixture is refluxed for 30 minutes on an oil bath. After cooling to room temperature, the resultant mixture is mixed with 0.5 g (1.82 mmol) of 3-cyano-9-(dimethylcarbamoylthio)-4-oxo-4H-pyrido[1,2-a]pyrimidine (I d-1) in the solid form and refluxed for 16 hours under heating. The resultant mixture is concentrated under reduced pressure, and water is added to the residue. The

TABLE 4

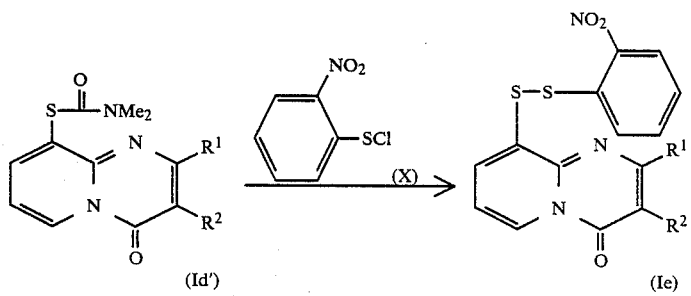

| Example No. | R$^1$ | R$^2$ | Amount I d' (g) | Amount X (g) | Amount ZnCl$_2$ (g) | Solvent (ml) | Reaction Time (min.) | Product (Yield) (%) | Melting Point (°C.) | Molecular Formula | Elementary Analysis (%) Found C | H | N | S |
|---|---|---|---|---|---|---|---|---|---|---|---|---|---|---|
| 44 | CH$_3$ | H | 0.7 | 0.56 | 0.4 | 15 | 60 | 92 | 225–227 | C$_{15}$H$_{11}$N$_3$O$_3$S$_2$ | 52.12 | 3.26 | 11.94 | 18.63 |
| | | | | | | | | | | | 52.16 | 3.21 | 12.17 | 18.56 |
| 45 | H | H | 0.7 | 0.5 | 0.4 | 15 | 60 | 92.9 | 253–255 | C$_{14}$H$_9$N$_3$O$_3$S$_2$ | 50.68 | 2.65 | 12.59 | 19.16 |
| | | | | | | | | | | | 50.75 | 2.74 | 12.68 | 19.35 |
| 46 | H | COOEt | 1.0 | 0.5 | 0.35 | 15 | 60 | 27.5 | −237 | C$_{15}$H$_9$N$_3$O$_6$S$_2$ | 47.78 | 2.48 | 10.94 | 17.26 |
| | | | | | | | | | | | 47.99 | 2.42 | 11.19 | 17.08 |
| 47 | H | CN | 0.7 | 0.5 | 0.4 | 15 | 32 | 92.6 | 251–252 | C$_{15}$H$_3$N$_4$O$_3$S$_2$ | 50.28 | 2.51 | 15.47 | 17.94 |
| | | | | | | | | | | | 50.56 | 2.26 | 15.72 | 17.99 |
| 48 | COOEt | CH$_3$ | 0.55 | 0.34 | 0.34 | 15 | 30 | 77.1 | 179–180 | C$_{18}$N$_{15}$N$_3$O$_5$S$_2$ | 51.77 | 3.78 | 9.80 | 15.12 |
| | | | | | | | | | | | 51.79 | 3.68 | 10.07 | 15.36 |

EXAMPLE 49

3-(1H-Tetrazole-5-yl)-9-(dimethylcarbamoylthio)-4-oxo-4H-pyrido[1,2-a]pyrimidine (I d-2)

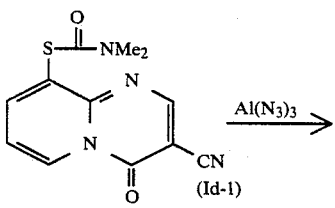

solution is acidified with 6N—HCl up to pH 2, and the crystals obtained are collected by filtration and washed with a small amount of tetrahydrofuran. The crystals obtained are dissolved in 5% of NaHCO$_3$ and the insolble material is filtered off. The filtrate is acidified with 6N—HCl, and the crystals obtained are collected by filtration and washed with a small amount of methanol to give 0.251 g (Yield: 43.4%) of the titled compound (I d-2).

m.p. 270°–274° C. (dec) (dimethyl sulfoxide-methanol).

Anal Calcd. (%) for $C_{12}H_{11}N_7O_2S$: C, 45.42; H, 3.49; N, 30.90; S, 10.10; Found (%): C, 45.14; H, 3.48; N, 30.89; S, 10.10.

EXAMPLE 50

3-(1H-Tetrazole-5-yl)-9-(phenylthiomethyl)-4-oxo-4H-pyrido[1,2-a]pyrimidine (I f-1)

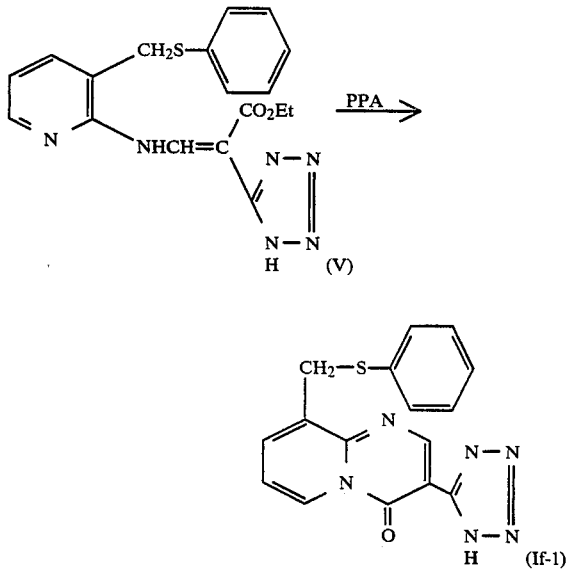

A mixture of 30.4 g (79.5 mmol) of ethyl 2-(1H-tetrazole-5-yl)-3-(3-phenylthiomethylpyridine-2-yl)aminoacrylate (V) in 300 g of polyphosphoric acid is heated at 110° C. for 1 hour under stirring. After cooling, the mixture is poured into 200 ml of water and adjusted to pH 5 with conc. aqueous ammonia. The solid obtained is collected by filtration, washed with water and ethyl acetate. Then the resultant residue is dissolved in tetrahydrofuran, and the insoluble material is filtered off. The filtrate is dried over $Na_2SO_4$ and concentrated under reduced pressure to give 4.169 g of light yellow powder, which is chromatographed on a column of silica gel eluting with tetrahydrofuran and ethyl acetate-methanol (1:1 v/v) to give 2.1 g of the titled compound (I f-1).

m.p. over 260° C. (methanol).

Anal Calcd. (%) for $C_{15}H_{12}N_6OS.3/2H_2O$: C, 51.27; H, 4.30; N, 23.92; S, 9.12; Found (%): C, 51.51; H, 4.18; N, 23.99; S, 9.28.

EXAMPLE 51

3-Ethoxycarbonyl-9-(thiomorpholinocarbonylthio)-4H-quinolizin-4-one (I a-6)

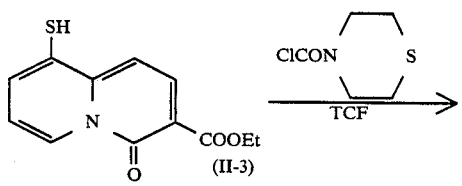

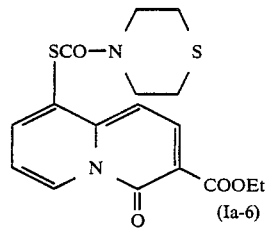

A mixture of 0.24 ml of trichloromethyl chloroformate (TCF) and 15 ml of tetrahydrofuran is stirred at 60° C. for 2 hours, cooled with ice, mixed with 412 mg of thiomorpholine, and the mixture is stirred for 1 hour at room temperature. The reaction mixture is cooled with ice again and mixed with 1.212 g of triethylamine. The mixture is stirred at room temperature for 1 hour, mixed with 500 mg of 3-ethoxycarbonyl-9-mercapto-4H-quinolizin-4-one (II-3), and the mixture is stirred at room temperature for 17 hours. The reaction mixture is filtered, and the filtrate is concentrated. The residue is chromatographed on a column of 10 g of silica gel, eluting with methylene chloride-methanol (19:1 v/v). The resultant crystals are recrystallized from ethyl acetate to give 321 mg (Yield: 42.3%) of 3-ethoxycarbonyl-9-(thiomorpholinocarbonylthio)-4H-quinolizin-4-one (I a-6).

m.p. 146°–148° C.

Anal Calcd. (%) for $C_{17}H_{18}N_2O_4S_2$: C, 53.95; H, 4.79; N, 7.40; S, 16.94; Found (%): C, 53.93; H, 4.82; N, 7.33; S, 16.96.

IR (Nujol): 1709, 1668, 1613, 1576, 1534 cm$^{-1}$.

NMR (CDCl$_3$) δ: 9.48 (1H, d, J=7 Hz); 8.45 (1H, d, J=9 Hz); 7.87 (1H, d, d, J=1.7 Hz); 7.16 (1H, m); 7.12 (1H, d, J=9 Hz); 4.41 (2H, q, J=7 Hz); ca. 3.90 (4H); ca. 2.72 (4H); 1.39 (3H, t, J=7 Hz).

EXAMPLE 52

3-Ethoxycarbonyl-9-(morpholinocarbonylthio)-4H-quinolizin-4-one (I a-7)

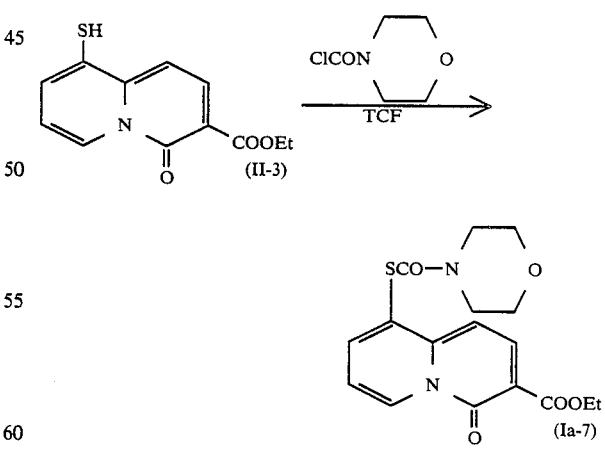

The reaction is performed as described in Example 51, whereby the objective compound (I a-7) is obtained.

Yield: 41.7%.

m.p. 207°–208° C.

Anal Calcd. (%) for $C_{17}H_{18}N_2O_5S$: C, 56.34; H, 5.01; N, 7.73; S, 8.85; Found (%): C, 56.27; H, 5.18; N, 7.69; S, 8.81.

IR (Nujol): 1704, 1669, 1613, 1576, 1535 cm$^{-1}$.

NMR (CDCl$_3$) δ: 9.47 (1H, d, J=7 Hz); 8.45 (1H, d, J=9 Hz); 7.87 (1H, d, d, J=1.7 Hz); 7.16 (1H, m); 7.12 (1H, d, J=9 Hz); 4.40 (2H, q, J=7 Hz); ca. 3.72 (4H); ca. 3.66 (4H); 1.38 (3H, t, J=7 Hz).

EXAMPLE 53

3-Ethoxycarbonyl-9-(2-nitrophenyldithio)-4-oxo-4H-pyrazino[1,2-a]pyrimidine (I e-2)

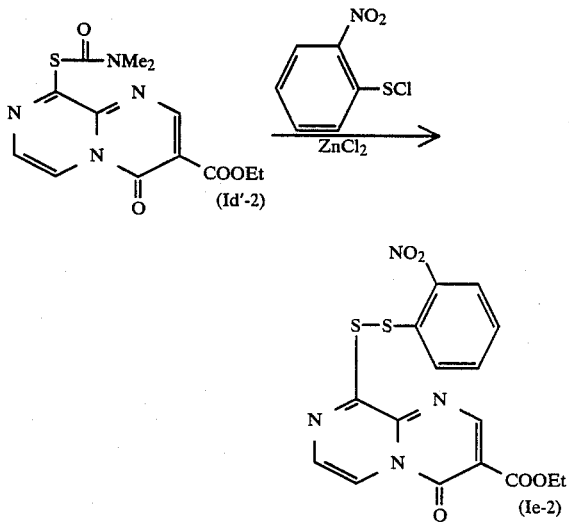

A mixture of 322 mg of Compound (I d'-2), 10 ml of dry 1,2-dichloroethane, 200 mg (1.05 eq) of 2-nitrobenzenesulfenyl chloride, and 200 mg (1.5 eq) of zinc chloride is stirred for 1 hour at room temperature and then refluxed for 1 hour. The reaction mixture is diluted with methylene chloride, washed with N—HCl, aqueous NaHCO$_3$ and brine successively, and the organic layer is dried over sodium sulfate and concentrated under reduced pressure. The residue is chromatographed on a column of 10 g of silica gel, eluting with methylene chloride-methanol (100:1 v/v). The eluate is concentrated and the residue is recrystallized from methylene chloride-ethyl acetate to give 354 mg (Yield: 87.6%) of Compound (I e-2).

m.p. 224°–226° C.

Anal Calcd. (%) for C$_{16}$H$_{12}$N$_4$O$_5$S$_2$: C, 47.52; H, 2.99; N, 13.85; S, 15.86; Found (%): C, 47.18; H, 3.13; N, 13.62; S, 16.08.

IR (Nujol): 1751, 1691, 1602, 1593, 1570 cm$^{-1}$.

NMR (CDCl$_3$) δ: 9.11 (1H, s); 8.69, 8.08 (each 1H, d, J=5 Hz); 8.32, 7.82 (each 1H, d, d, J=8,2 Hz); ca. 7.52 (2H); 4.45 (2H, q, J=7 Hz); 1.42 (3H, t, J=7 Hz).

EXAMPLE 54

3-Ethoxycarbonyl-9-propylthio-4-oxo-4H-pyrazino[1,2-a]pyrimidine (I e-3)

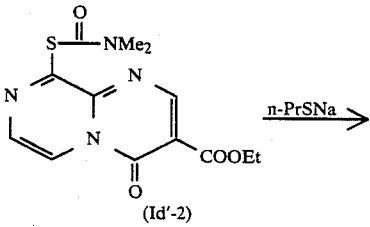

-continued

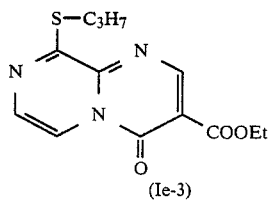

To a mixture of 34 mg (1.2 eq) of 50% NaH dispersion (mineral oil) and 59 mg (1.1 eq) of n-PrSH in 2 ml of dry tetrahydrofuran is added a solution of 229 mg of Compound (I d'-2) in 4 ml of THF in one portion. The mixture is stirred at room temperature for 18 hours. The reaction mixture is mixed with 2 ml of aqueous sodium hypochlorite and extracted with methylene chloride. The organic layer is washed with water, dried over Na$_2$SO$_4$ and concentrated to give 283 mg of residue, which is chromatographed on a column of 4 g of silica gel. The fraction eluted with ethyl acetate is concentrated and recrystallized from ethyl acetate-hexane to give 124 mg (Yield: 59.7%) of 3-ethoxycarbonyl-9-propylthio-4-oxo-4H-pyrazino[1,2-a]pyrimidine (I e-3).

m.p. 112° C.

Anal Calcd. (%) for C$_{13}$H$_{15}$N$_3$O$_3$S: C, 52.23; H, 5.15; N, 14.32; S, 10.93; Found (%): C, 52.85; H, 5.12; N, 14.23; S, 10.62.

Mass: M+ m/z 293.

IR (Nujol): 3132, 1761, 1743, 1688, 1597 cm$^{-1}$.

NMR (CDCl$_3$) δ: 9.02 (1H, s); 8.55, 8.06 (each 1H, d, J=5 Hz); 4.40 (2H, q, J=7 Hz); 3.20 (2H, t, J=7 Hz); 1.70 (2H, m); 1.40, 1.07 (each 3H, t, J=7 Hz).

EXAMPLE 55

3-Ehtoxycarbonyl-9-[(3,4-dichlorophenyl)carbohydroxymoylthio]-4H-quinolizin-4-one (I b-2)

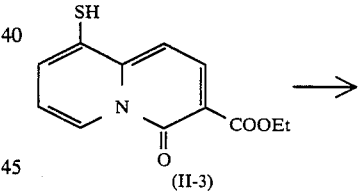

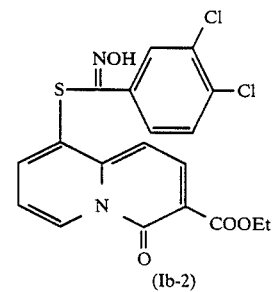

9-Mercapto-3-ethoxycarbonyl-4H-quinolizin-4-one (II-3) is allowed to react in the same manner as in Example 24 to give the titled compound (I b-2).

Yield: 72.1%, m.p. 225°–227° C.

Anal Calcd. (%) for C$_{19}$H$_{14}$Cl$_2$N$_2$O$_4$S: C, 52.19; H, 3.23; N, 6.41; Cl, 16.21; S, 10.93; Found (%): C, 52.15; H, 3.32; N, 6.40; Cl, 16.03; S, 7.47.

IR (Nujol): 3325, 1721, 1641, 1628, 1587, 1574 cm$^{-1}$.

NMR (DMSO-d$_6$) δ: 12.32 (1H, s); 9.21 (1H, d, J=7 Hz); 8.30 (1H, s); 8.07–7.96 (2H); 7.49 (1H, m); 7.37 (1H, d, J=2 Hz); 7.32 (1H, d, J=9 Hz); 7.05 (1H, d, d, J=2, 9 Hz); 4.22 (2H, q, J=7 Hz); 1.30 (3H, t, J=7 Hz).

REFERENCE EXAMPLE 1

3-Ethoxycarbonyl-9-mercapto-4-oxo-4H-pyrido[1,2-a]pyrimidine (II-1)

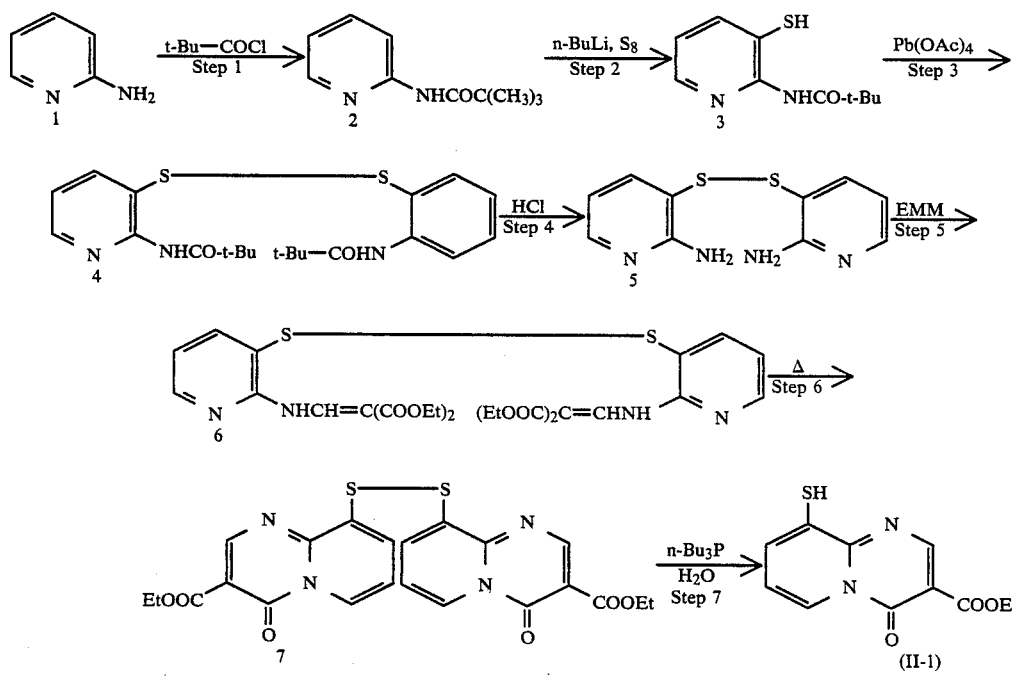

Step 1

To a solution of 20 g (0.21 mol) of 2-aminopyridine and 26.9 g (0.26 mmol) of triethylamine in 300 ml of dry methylene chloride is dropwise added a solution of 28.2 g (0.23 ml) of pivaloyl chloride in 40 ml of dry methylene chloride under cooling. The mixture is stirred at room temperature for 2.5 hours. Into 400 ml of water is poured the reaction mixture, and the organic layer is washed with 5% NaHCO3 and water in order, dried over sodium sulfate and concentrated under reduced pressure to give 43.2 g of crude product 2. The crude product 2 is chromatographed on a column of silica gel eluting with ethyl acetate to give 23.3 g (Yield: 61.5%) of Compound 2.

m.p. 67°-69° C. (colorless crystals, from n-hexane)

Step 2

To a solution of Compound 2 obtained above in 30 ml of dry tetrahydrofuran cooled at −60° to −65° C. is dropwise added 18 ml of 1.6M solution of n-butyllithium (n-BuLi) in n-hexane with a syringe. The mixture is stirred for 3 hours in an ice-water bath, cooled to −60° to −65° C. again, mixed with 0.4 g of sulfur in the solid form, and stirred for 1 hour at the same temperature. Then, the mixture is stirred for 30 minutes under ice-cooling and concentrated to dryness under reduced pressure to give a residue, which is dissolved in 150 ml of water. The aqueous solution is acidified with acetic acid to pH 4–5 and extracted with ethyl acetate. After the organic layer is dried over Na2SO4, the solvent is evaporated under reduced pressure. The resultant solid is washed with ethyl ether to give 1.48 g (Yield: 62.7%) of Compound 3.

m.p. 164°-169° C. (yellow crystals, from chloroform-n-hexane).

Anal Calcd. (%) for $C_{10}H_{14}N_2OS$: C, 57.11; H, 6.71; N, 13.32; S, 15.25; Found (%): C, 57.01; H, 6.70; N, 13.16; S, 15.18.

Step 3

To a solution of 3.9 g (8.8 mmol) of lead tetraacetate in 60 ml of methylene chloride is dropwise added a solution of 3.0 g (14 mmol) of Compound 3 obtained above in 35 ml of methylene chloride, and the resultant mixture is stirred at room temperature for 30 minutes. The resultant suspension is filtered, and the precipitate is washed with methylene chloride. The filtrate is washed with 5% NaHCO3 and water in order, and dried over Na2SO4, and concentrated under reduced pressure to give a solid residue, which is washed with ethyl acetate to give 2.783 g (Yield: 93.2%) of Compound 4 as a white solid.

Step 4

A solution of 0.2 g of Compound 4 obtained above in 4 ml of 6N.HCl is refluxed for 2 hours. The reaction mixture is cooled, basified with conc. NH4OH to pH 11 and extracted with ethyl acetate. After the organic layer is dried over Na2SO4, it is concentrated under reduced pressure to give a solid residue, which is washed with ethyl ether to give 55 mg (Yield: 46%) of Compound 5 as yellow prisms.

m.p. 158°-160° C. (dec.)

Anal Calcd. (%) for $C_{10}H_{10}N_4S_2$: C, 47.97; H, 4.03; N, 22.38; S, 25.62; Found (%): C, 48.12; H, 3.98; N, 22.08; S, 25.54.

Step 5

A mixture of 0.1 g (0.4 mmol) of Compound 5 and 0.24 g (1.1 mmol) of diethyl ethoxymethylenemalonate is stirred at 100°-110° C. for 3 hours. After cooling to room temperature, the resultant mixture is mixed with n-hexane for crystallization to give 0.148 g (Yield: 62.7%) of Compound 6.

m.p. 119°-121° C. (light yellowish scaly crystals from chloroform-ethyl ether).

Anal Calcd. (%) for $C_{26}H_{30}N_4O_8S_2 \cdot 1/5Et_2O$: C, 53.16; H, 5.33; N, 9.25; S, 10.59; Found (%): C, 52.97; H, 5.15; N, 9.25; S, 10.44.

Step 6

A solution of 0.09 g (0.15 mmol) of Compound 6 obtained above in 4 ml of Dowtherm A is refluxed for 5 minutes and cooled to room temperature. The reaction mixture is chromatographed on a column of about 5 g of silica gel eluting with n-hexane to remove Dowtherm A and then eluting with ethyl acetate to give 0.051 g (Yield: 67.1%) of Compound 7.

m.p. 262°-264° C. (dec) (chloroform-n-hexane).

Anal Calcd. (%) for $C_{12}H_{10}O_3NS$: C, 58.05; H, 4.06; N, 5.64; S, 12.91 Found (%): C, 57.89; H, 4.15; N, 5.60; S, 12.73.

Step 7

To a solution of 1.0 g (2 mmol) of Compound 7 obtained above in 30 ml of chloroform are added 0.41 g (2 mmol) of n-Bu$_3$P and 1 ml of H$_2$O, and the mixture is refluxed for 1 hour under stirring. The reaction mixture is cooled to room temperature and extracted with 5% aqueous NaHCO$_3$. After washing with chloroform, the aqueous layer is acidified with conc. HCl to pH 2 to give a colorless precipitate, which is taken up in chloroform. The organic layer is washed with brine, dried over Na$_2$SO$_4$ and concentrated under reduced pressure to give crystals, which are washed with a small quantity of ethyl acetate to give 0.54 g (Yield: 53.8%) of Compound (II-1).

m.p. 151°-152° C. (ethyl acetate).

Anal Calcd. (%) for $C_{11}H_{10}N_2O_3S$: C, 52.79; H, 4.03; N, 11.19; S, 12.81; Found (%): C, 52.88; H, 3.97; N, 11.24; S, 12.66.

REFERENCE EXAMPLE 2

3-Cyano-9-hydroxy-4-oxo-4H-pyrido[1,2-a]pryimidine (VI-1)

poured into 1.2 l of ice water and the precipitated crystals are collected by filtration. The crystals obtained are washed with a small quantity of methanol and dried to give 95.7 g (Yield: 84%) of Compound 10 as darkish black crystals.

Step 2

A suspension of 42.25 g (240 mmol) of Compound 10 obtained above in the mixture of 100 ml of conc. HCl and 500 ml of ethanol is stirred at room temperature for 60 hours. The precipitate is collected by filtration and washed with a small quantity of ethanol to give 49.3 g (91.2%) of the hydrochloride 11.

Step 3

A suspension of 48.3 g (0.21 mol) of hydrochloride obtained above 11 in 500 ml of water is refluxed for 1 hour with stirring on an oil bath. The mixture is cooled to room temperature and the filtrate is extracted with ethyl acetate. The organic layer is dried and concentrated under reduced pressure to give 14.28 g (35.3%) of Compound (VI-1).

REFERENCE EXAMPLE 3

3-Ethoxycarbonyl-9-mercapto-4H-quinolizin-4-one (II-3)

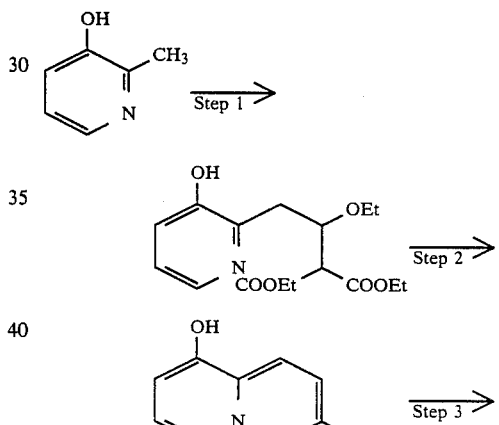

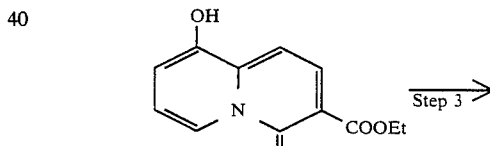

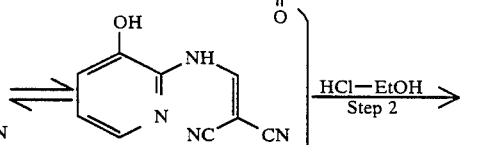

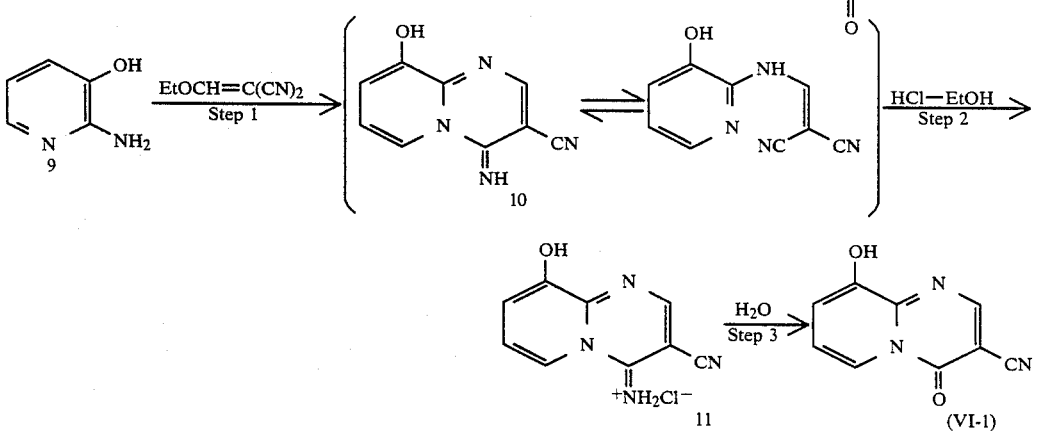

Step 1

To a suspension of 67 g (0.61 mol) of 2-amino-3-hydroxypyridine in 200 ml of dry dimethylformamide is added 73.1 g (0.6 mol) of ethoxymethylenemalononitrile, and the mixture is stirred at 110° C. under heating for 3 hours in an oil bath. The reaction mixture is -continued

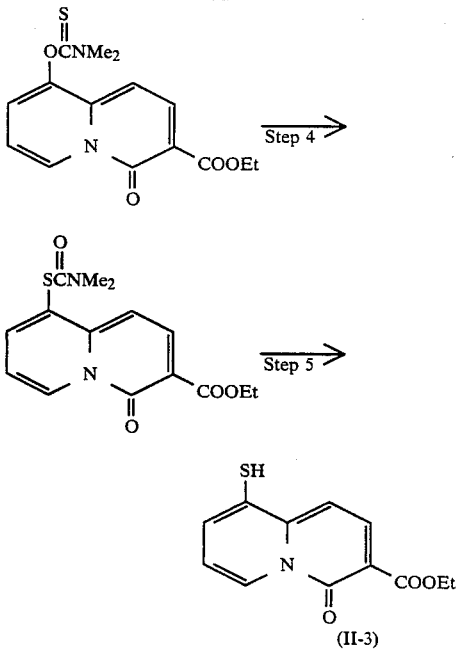

Step 1

To a solution of 5.47 g of 3-hydroxy-2-methylpyridine in 218 ml of tetrahydrofuran is added 69 ml of a 1.6M solution of n-butyllithium in n-hexane under cooling at −30° C. The resulting darkish red solution is stirred at room temperature for 1 hour. The solution is cooled to −70° C. and a solution of 11.92 g of diethyl ethoxymethylenemalonate in 12 ml of tetrahydrofuran is added over 30 minutes. The reaction mixture is stirred at 0° C. for 30 minutes. The mixture is mixed with 10 ml of acetic acid and concentrated, and the residue is dissolved in ethyl acetate. The organic layer is washed with 10% NaHCO₃, water and saturated aqueous sodium chloride in order, dried over sodium sulfate, and concentrated to give 17.2 g of ethyl 3-ethoxy-2-ethoxycarbonyl-4-[2-(3-hydroxypyridyl)]butyrate as an oil.

NMR (CDCl₃) δ: 8.06 (1H, d, d, J=1.5, 4 Hz); 7.27–6.99 (2H); 4.51–4.05 (5H); 3.78–3.41 (3H); 3.26 (2H, t, J=5 Hz); 1.27 (2×3H, t, J=7 Hz); 1.13 (3H, t, J=7 Hz).

Step 2

A mixture of 17.2 g of ethyl 3-ethoxy-2-ethoxycarbonyl-4-[2-(3-hydroxypyridyl)]butyrate and 100 ml of diphenyl ether is refluxed for 5 minutes. The reaction mixture is cooled to room temperature and chromatographed on a column of 170 g of silica gel eluting with n-hexane and a mixture of methylene chloride and methanol (93:7 v/v) to give crude product. It is recrystallized from ethyl acetate to give 74.74 g (Yield: 63.9%) of 3-ethoxycarbonyl-9-hydroxy-4H-quinolizin-4-one.

m.p. 236°–238° C. (dec)

Anal Calcd. (%) for C₁₂H₁₁NO₄: C, 61.80; H, 4.75; N, 6.01; Found (%): C, 61.74; H, 4.78; N, 5.89.

IR (Nujol): 3220 (br); 1722, 1642, 1621, 1587, 1512 cm⁻¹.

NMR (CDCl₃-CD₃OD, 9:1) δ: 8.90 (1H, d, d, J=2.5 Hz); 8.32, 7.12 (each 1H, d, J=9 Hz); 7.05 (2×1H, m); 4.38 (2H, q, J=7 Hz); 3.42 (1H, br); 1.41 (3H, t, J=7 Hz).

Step 3

A mixture of 7.474 g of 3-ethoxycarbonyl-9-hydroxy-4H-quinolizin-4-one, 4.77 g of dimethylthiocarbamoyl chloride, 4.897 g of triethylamine and 394 mg of 4-dimethylaminopyridine in 230 ml of acetone is stirred at room temperature for 20 hours. The reaction mixture is filtered to remove the insoluble material, and the filtrate is concentrated in vacuo. The residue is dissolved in ethyl acetate, and the solution is washed with water and saturated brine in order, dried over sodium sulfate, and concentrated in vacuo. The residue is chromatographed on a column of 60 g of silica gel eluting with ethyl acetate to give crude product. It is recrystallized from ethyl acetate to give 6.483 g (Yield: 63.2%) of 3-ethoxycarbonyl-9-dimethylthiocarbonyloxy-4H-quinolizin-4-one.

m.p. 186°–188° C.

Anal Calcd. (%) for C₁₅H₁₆N₂O₄S: C, 56.24; H, 5.03; N, 8.74; S, 10.01; Found (%): C, 55.77; H, 5.04; N, 8.63; S, 9.78.

IR (Nujol): 1737, 1666, 1632, 1587 cm⁻¹.

NMR (CDCl₃) δ: 9.30, 7.32, 7.17 (each 1H, m); 8.38, 6.60 (each 1H, d, J=9 Hz); 4.39 (2H, q, J=7 Hz); 3.50, 3.48 (each 3H, s); 1.40 (3H, t, J=7 Hz).

Step 4

A mixture of 6.483 g of 3-ethoxycarbonyl-9-dimethylthiocarbamoyloxy-4H-quinolizin-4-one and 36 ml of diphenyl ether is refluxed for 10 minutes. The reaction mixture is cooled to room temperature and chromatographed on a column of 50 g of silica gel eluting with n-hexane and a mixture of methylene chloride and methanol (97:3 v/v) to give crude product, which is recrystallized from ethyl acetate to give 5.847 g (Yield: 90.2%) of 3-ethoxycarbonyl-9-dimethylcarbamoylthio-4H-quinolizin-4-one.

m.p. 119°–121° C.

Anal Calcd. (%) for C₁₅H₁₆N₂O₄S: C, 56.24; H, 5.03; N, 8.74; S, 10.01; Found (%): C, 56.24; H, 5.04; N, 8.69; S, 9.86.

IR (Nujol): 1746, 1684, 1615, 1574, 1536 cm⁻¹.

NMR (CDCl₃) δ: 9.47 (1H, d, J=7 Hz); 8.44 (1H, d, J=9 Hz); 7.87 (1H, d, d, J=1.5, 7 Hz); ca. 7.15 (2H, m); 4.41 (2H, q, J=7 Hz); 3.11 (2×3H, br, s); 1.38 (3H, t, J=7 Hz).

Step 5

To a suspension of 0.395 g of 60% sodium hydride (mineral oil dispersion) in 20 ml of anhydrous tetrahydrofuran is added 0.82 ml of n-propyl mercaptan under ice-cooling. After stirring for 30 minutes, the resultant mixture is mixed with 2.634 g of 3-ethoxycarbonyl-9-dimethylcarbamoylthio-4H-quinolizin-4-one in 40 ml of tetrahydrofuran, and stirred at room temperature for another 15 hours. The reaction mixture is mixed with 8 ml of aqueous sodium hypochlorite and extracted with methylene chloride. The organic layer is washed with water, dried over sodium sulfate and concentrated to give a residue, which is chromatographed on a column of 30 g of silica gel eluting with methylene chloride-methanol (9:1 v/v) to give crude product, which is recrystallized from ethyl acetate to give 1.153 g (Yield: 56.3%) of 3-ethoxycarbonyl-9-mercapto-4H-quinolizin-4-one.

m.p. 111°–113° C.

Anal Calcd. (%) for $C_{12}H_{11}NO_3S \cdot 1/10H_2O$: C, 57.40; H, 4.50; N, 5.58; S, 12.77; Found (%): C, 57.24; H, 4.38; N, 5.58; S, 12.49.

IR (Nujol): 3068, 2548, 1733, 1651, 1642, 1617, 1575, 1531 cm$^{-1}$.

NMR (CDCl$_3$) δ: 9.25 (1H, d, J=8 Hz); 8.41 (1H, d, J=9 Hz); 7.67 (1H, d, d, J=1,7 Hz); 7.01 (1H, m); 6.88 (1H, d, J=9 Hz); 4.39 (2H, q, J=7 Hz); 3.77 (1H, br); 1.40 (3H, t, J=7 Hz).

REFERENCE EXAMPLE 4

3-Ethoxycarbonyl-9-hydroxy-4-oxopyrazino[1,2-a]pyrimidine

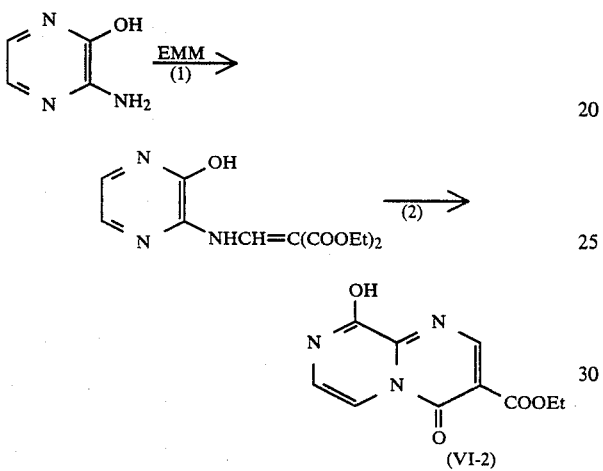

(1) A mixture of 1.645 g of 2-amino-1-hydroxypyrazine and 7.736 g of EMM is stirred at 110° C. for 2 hours. The reaction mixture is dissolved in methylene chloride-methanol (9:1 v/v) and chromatographed on a column of 50 g of silica gel. The eluate is concentrated and recrystallized from methylene chloride-ethanol to give 3.187 g (Yield: 76.5%) of diethyl N-(3-hydroxypyrazine-2-yl)aminomethylenemalonate.

Anal Calcd. (%) for $C_{12}H_{15}N_3O_5$: C, 51.24; H, 5.38; N, 14.94; Found (%): C, 51.00; H, 5.37; N, 14.90.

IR (Nujol): 3232, 3088, 1695, 1668, 1656, 1620, 1593, 1533 cm$^{-1}$.

NMR (CDCl$_3$-CD$_3$OD) δ: 8.92 (1H, s); 7.14, 6.96 (each 1H, d, J=4 Hz); 4.35, 4.27 (each 2H, q, J=7 Hz); 3.68 (2H, br.s, —NH, —OH); 1.37, 1.33 (each 3H, t, J=7 Hz).

(2) A mixture of 3.738 g of diethyl N-(3-hydroxypyrazine-2-yl)-aminomethylenemalonate obtained above and 70 ml of Dowtherm A is refluxed for 10 minutes. The reaction mixture is cooled to room temperature and mixed with 200 ml of n-hexane. The precipitated crystals are collected by filtration to give 3.00 g (Yield: 96.2%) of Compound (VI-2).

m.p. over 300° C.

Anal Calcd. (%) for $C_{10}H_9N_3O_4$: C, 51.07; H, 3.86; N, 17.87; Found (%): C, 51.07; H, 3.78; N, 17.88.

IR (Nujol): 3128 (sh), 3056 (sh), 1723, 1691, 1657, 1579, 1505 cm$^{-1}$.

NMR (CF$_3$COOH) δ: 9.15 (1H, s); 8.10, 7.71 (each 1H, d, J=6 Hz); 4.60 (2H, q, J=7 Hz); 1.51 (3H, t, J=7 Hz).

REFERENCE EXAMPLE 5

3-Ethoxycarbonyl-9-dimethylcarbamoylthio-4-oxo-4H-pyrazino[1,2-a]pyrimidine (I d'-2)

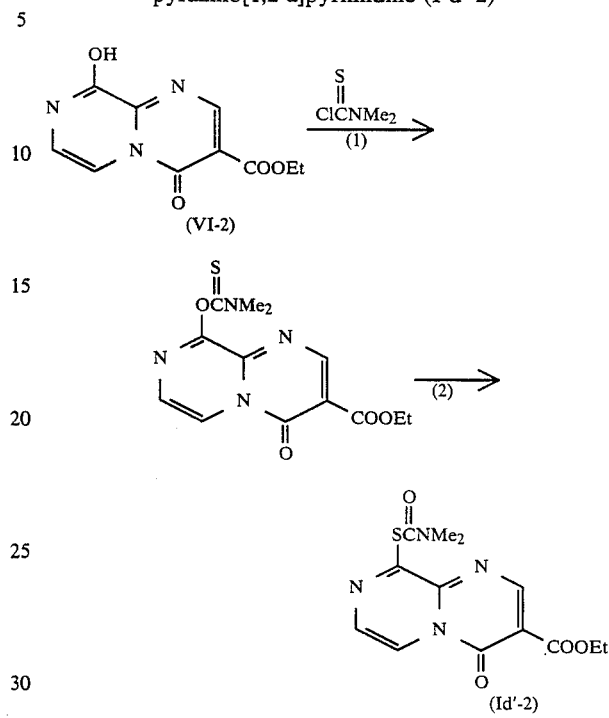

(1) To a suspension of 2.40 g of 3-ethoxycarbonyl-9-hydroxy-4H-4-oxo-pyrazino[1,2-a]pyrimidine (VI-2) in 80 ml of HMPA are added 817 mg of 60% NaH (mineral oil dispersion) and 2.513 g of dimethylcarbamoyl chloride, and the resultant mixture is stirred at room temperature for 16 hours. The reaction mixture is mixed with 200 ml of water to give crystals. The crystals are collected by filtration and dissolved in a mixture of methylene chloride-methanol (9:1 v/v). The insolble material (VI-2) in 877 mg (36.5%) is filtered off. The filtrate is concentrated to give a residue, which is chromatographed on a column of 20 g of silica gel to give 1.029 g (Yield: 31.3%) of 3-ethoxycarbonyl-9-dimethylthiocarbamoyloxy-4H-oxopyrazino-[1,2-a]pyrimidine after recrystallization from methylene chloride-ethyl acetate.

m.p. 164°-166° C.

Anal Calcd. (%) for $C_{13}H_{14}N_4O_4S$: C, 48.44; H, 4.38; N, 17.38; S, 9.95; Found (%): C, 48.44; H, 4.30; N, 17.27; S, 9.99.

IR (Nujol): 3136, 1755, 1677, 1617, 1569, 1507 cm$^{-1}$.

NMR (CDCl$_3$) δ: 9.08 (1H, s); 8.86, 8.07 (each 1H, d, J=5 Hz); 4.43 (2H, q, J=7 Hz); 3.50, 3.47 (each 3H, s); 1.39 (3H, t, J=7 Hz).

(2) A mixture of 929 mg of the compound obtained above and 10 ml of Dowtherm A is refluxed for 10 minutes. The reaction mixture is cooled to room temperature and chromatogaraphed on a column of 20 g of silica gel eluting with n-hexane and a mixture methylene-chloride-methanol (19:1 v/v) to give 845 mg of crude product, which is recrystallized from ethyl acetate to give 185 mg (Yield: 27.4%, m.p. 255°-258° C.) of 9-bis(3-ethoxycarbonyl-4H-4-oxo-pyrazino[1,2-a]pyrimidine) sulfide.

Then the mother liquor obtained above is subjected to a column of 20 g of silica gel, which is eluted first with a mixture of n-hexane-ethyl acetate (1:1 v/v) and then ethyl acetate only. The n-hexane-ethyl acetate eluent is recrystallized from ethyl acetate-n-hexane to give 212 mg (Yield: 28.0%) of 3-ethoxycarbonyl-9-dimethylamino-4H-4-oxopyrazino[1,2-a]pyrimidine (m.p. 98°–99° C.). Then, the eluate with ethyl acetate only is concentrated and recrystallized from ethyl acetate-n-hexane to give 266 mg (Yield: 28.6%) of the title compound (I d'-2).

m.p. 125°–128° C.

Anal Calcd. (%) for $C_{13}H_{14}N_4O_4S$: C, 48.44; H, 4.38; N, 17.38; S, 9.95; Found (%): C, 48.55; H, 4.26; N, 17.11; S, 9.58.

IR (Nujol): 1762, 1739, 1682, 1600, 1553 cm$^{-1}$.

NMR (CDCl$_3$) δ: 9.12 (1H, s); 8.87, 8.31 (each 1H, d, J=5 Hz); 4.44 (2H, q, J=7 Hz); 3.18 (2×3H, br, s); 1.40 (3H, t, J=7 Hz).

FORMULATION

| | |
|---|---|
| 3-Ethoxycarbonyl-9-(4-morpholinothio)-4-oxo-4H-pyrido[1,2-a]pyrimidine (Ia-1) | 25 mg |
| Lactose | 100 mg |
| Wheat Starch | 15 mg |
| Gelatin | 5 mg |
| Magnesium stearate | 5 mg |
| Total | 150 mg |

Thease materials are charged in a capsule, whereby the capsule is obtained.

EXPERIMENT 1 (EFFECT ON STRESS ULCER)

Test method

Male SD rats (body weight: 260–290 g) which had fasted for 24 hours were placed in a wire net-restraint cage and immersed up to the breast in water at 23° C. After 7 hours, the animals were sacrificed, and the stomach were excised. Then the sum of length of ulcer which occurred in gastric glandular region was found and the inhibition of ulcer occurrence was calculated by comparing with the control group. The test compound was suspended in 5% gum arabic solution and orally administered 30 minutes before the stress load.

Test compounds

Compound numbers shown in the table of results correspond to those used in the examples. Cimetidine was used as control drug. The result is shown in Table 5.

TABLE 5

| Dose (mg/kg) | Inhibition rate (%) Test Compound | | | | | | | Reference Cimetidine |
|---|---|---|---|---|---|---|---|---|
| | 7 | 9 | 13 | 14 | 16 | 17 | 18 | 19 | |
| 1 | | | | 45 | | | | | |
| 3 | 46 | 33 | 34 | 50 | 40 | 74 | 80 | | |
| 10 | 77 | 66 | 70 | 68 | 62 | 72 | 76 | 45 | |
| 30 | 71 | 80 | 81 | 89 | 85 | 70 | | | 56 |

From the above-mentioned results it is evident that the antiulcer activity of the compounds (I) of this invention was about ten times as potent as that of control drug. Results of acute toxicity test by administering intraperitoneally the compounds of the present invention (Example No. 7, 14 and 17) to mice (n=5—6) showed no dead case even at a dose of 500 mg/kg. And the compounds (I) of the present invention exhibit remarkable antiulcer activity against various exprimental ulcers and have the features mentioned below.

1. The compounds of the present invention are useful as antiulcer agent of non-antisecretory gastroprotective type.

2. The compounds of the present invention exhibit more excellent antiulcer activity in oral route than known compounds.

Accordingly, the compounds of the present invention are effective for the treatment and prophylaxis of gastrointestinal ulcers.

What we claim is:

1. A compound of the formula:

wherein
R$^1$ and R$^2$ each is hydrogen, methyl, ethyl, methoxycarbonyl, or ethoxycarbonyl; R$^3$ and R$^4$, which may be bound to any of P, Q, and W, each is hydrogen, methyl, ethyl, methoxycarbonyl, ethoxycarbonyl, piperonyl, phenyl, methoxyphenyl, or α-phenyl-4-chlorobenzyl, or R$^3$ and R$^4$ taken together may form a condensed benzene ring; P and Q each is methylene or ethylene; W is single bond or —O—, —S—, or imino, or a pharmaceutically acceptable acid addition salt thereof.

2. The compound claimed in claim 1, namely 3-ethoxycarbonyl-9-(4-morpholinocarbonylthio)-4-oxo-4H-pyrido[1,2-a]pyrimidine.

3. The compound claimed in claim 1, namely 3-ethoxycarbonyl-9-[(1-(2-methoxyphenyl)piperazin-4-yl)carbonylthio]-4-oxo-4H-pyrido[1,2-a]pyrimidine.

4. The compound claimed in claim 1, namely 2-ethoxycarbonyl-3-methyl-9-[(4-morpholinocarbonylthio)-4-oxo-4H-pyrido[1,2-a]-pyrimidine.

5. The compound claimed in claim 1, namely 3-ethoxycarbonyl-9-[(thiomorpholin-4-yl)carbonylthio]-4-oxo-4H-pyrido[1,2-a]-pyrimidine.

6. The compound claimed in claim 1, namely 3-ethoxycarbonyl-9-[(4-piperonylpiperazin-1-yl)carbonylthio]-4-oxo-4H-pyrido[1,2-a]-pyrimidine.

7. The compound claimed in claim 1, namely 9-[(4-isopropyl-carbamoylpiperazin-1-yl)carbonylthio]-4-oxo-4H-pyrido[1,2-a]-pyrimidine.

8. The compound claimed in claim 1, namely 9-[(4-thiomorpholin-4-yl)carbonylthio]-4-oxo-4H-pyrido[1,2-a]pyrimidine.

9. The compound claimed in claim 1, namely 9-[(benzothiazin-4-yl)carbonylthio]-4-oxo-4H-pyrido[1,2-a]pyrimidine.

10. The compound claimed in claim 1, namely 9-[(morpholin-4-yl)-carbonylthio]-4-oxo-4H-pyrido[1,2-a]pyrimidine.

11. The compound claimed in claim 1, namely 9-(isoindolinylcarbonylthio)-4-oxo-4H-pyrido[1,2-a]pyrimidine.

12. The compound claimed in claim 1, namely 9-[(4-(2-methoxyphenylpiperazin-1-yl)carbonylthio]-4-oxo-4H-pyrido[1,2-a]pyrimidine.

13. The compound claimed in claim 1, namely 9-[(4-(4-chloro-α-phenylbenzyl)piperazin-1-yl)carbonylthio]-4-oxo-4H-pyrido[1,2-a]pyrimidine.

14. The compound claimed in claim 1, namely 3-ethoxycarbonyl-9-(piperazin-1-yl-carbonylthio)-4-oxo-4H-pyrido[1,2-a]pyrimidine.

15. The compound claimed in claim 1, namely 3-ethoxycarbonyl-9-[(thiazolizin-3-yl)carbonylthio]-4-oxo-4H-pyrido[1,2-a]pyrimidine.

16. The compound claimed in claim 1, namely 3-ethoxycarbonyl-9-[(tetrahydroisoquinolin-2-yl)carbonylthio]-4-oxo-4H-pyrido[1,2-a]pyrimidine.

17. The compound claimed in claim 1, namely 3-ethoxycarbonyl-9-[(pyrrolidin-1-yl)carbonylthio]-4-oxo-4H-pyrido[1,2-a]pyrimidine.

18. The compound claimed in claim 1, namely 9-[(thiazolidin-3-yl)carbonylthio]-4-oxo-4H-pyrido[1,2-a]pyrimidine.

19. The compound claimed in claim 1, namely 9-(piperazinylcarbonylthio)-4-oxo-4H-pyrido[1,2-a]pyrimidine.

20. The compound claimed in claim 1, namely 9-[(pyrrolidin-1-yl)carbonylthio]-4-oxo-4H-pyrido[1,2-a]pyrimidine.

21. The compound claimed in claim 1, namely 3-ethoxycarbonyl-9-[(2,6-dimethylmorpholin-4-yl)carbonyl]-4-oxo-4H-pyrido[1,2-a]pyrimidine.

22. The compound claimed in claim 1, namely 3-ethoxycarbonyl-9-[(2-ethylmorpholin-4-yl)carbonyl]-4-oxo-4H-pyrido[1,2-a]pyrimidine.

23. The compound claimed in claim 1, namely 3-ethoxycarbonyl-9-[(1-4-methoxycarbonylthiazolidin-3-yl)carbonylthio]-4-oxo-4H-pyrido[1,2-a]pyrimidine.

24. The compound claimed in claim 1, namely 9-[(1-4-methoxycarbonylthiazolidin-3-yl)carbonylthio]-4-oxo-4H-pyrido[1,2-a]pyrimidine.

25. Anti-ulcer agent comprising a pharmacologically effective amount of the compound according to claim 1 as an active ingredient.

* * * * *